US008308727B2

(12) United States Patent
Hernandez et al.

(10) Patent No.: US 8,308,727 B2
(45) Date of Patent: Nov. 13, 2012

(54) FLEXIBLE TOOLING FOR USE IN MAXILLARY SINUS ELEVATION PROCEDURES AND METHOD OF USING THE SAME

(75) Inventors: Ernesto Hernandez, Weston, FL (US); Ronald G. Litke, Jr., Danbury, CT (US); Mark James DeBisschop, Burlington, CT (US); Antonio Jose Gordils Wallis, 5ta Mochi Caracas (VE)

(73) Assignee: Innovative Implant Technology, LLC, Weston, FL (US)

( * ) Notice: Subject to any disclaimer, the term of this patent is extended or adjusted under 35 U.S.C. 154(b) by 1118 days.

(21) Appl. No.: 12/195,944

(22) Filed: Aug. 21, 2008

(65) Prior Publication Data
US 2009/0181343 A1 Jul. 16, 2009

Related U.S. Application Data

(63) Continuation-in-part of application No. PCT/US2008/052578, filed on Jan. 31, 2008, and a continuation-in-part of application No. PCT/US2008/057421, filed on Mar. 19, 2008.

(60) Provisional application No. 60/909,240, filed on Mar. 30, 2007.

(51) Int. Cl.
*A61F 2/46* (2006.01)
(52) U.S. Cl. ........................... 606/86 R; 606/79
(58) Field of Classification Search ............... 606/86 R, 606/91–93
See application file for complete search history.

(56) References Cited

U.S. PATENT DOCUMENTS

| 4,340,060 A | * | 7/1982 | Berke et al. ............... 606/172 |
|---|---|---|---|
| 4,456,010 A | | 6/1984 | Reimels et al. |
| 4,600,006 A | | 7/1986 | Baker |
| 4,682,951 A | | 7/1987 | Linkow |
| 4,699,550 A | | 10/1987 | Baker |
| 4,803,982 A | | 2/1989 | Baker |
| 4,820,306 A | | 4/1989 | Gorman et al. |

(Continued)

FOREIGN PATENT DOCUMENTS

DE 3503098 C2 3/1994

(Continued)

OTHER PUBLICATIONS

The Sinus Lift Graft: Basic Technique and Variations, Dennis G. Smiler, Pract Periodontics Aesthet Dent 9(8):885-893 (1997).

(Continued)

*Primary Examiner* — Nicholas Woodall
(74) *Attorney, Agent, or Firm* — Gordon & Jacobson, PC

(57) ABSTRACT

Tooling and methodologies for separation and dissection of the subantral membrane from the floor of the maxillary sinus, and for packing bone and bone substitutes under the subantral membrane. The tooling and associated methodology employ a handle and one or more support structures extending therefrom. A thin member extends from the distal end of the support structure(s). The thin member has a first peripheral region disposed opposite a second peripheral region. The first peripheral region is joined to or integrally formed with the distal end of the support structure(s). The second peripheral region defines a thin blade-like section for dissecting the subantral membrane from the floor of the maxillary sinus. In the preferred embodiment, the blade-like section is angled downward away from the distal support structure, which aids in positioning the blade-like section on the floor of the maxillary sinus.

25 Claims, 27 Drawing Sheets

U.S. PATENT DOCUMENTS

| | | | |
|---|---|---|---|
| 4,884,571 A | 12/1989 | Baker | |
| 4,934,352 A * | 6/1990 | Sullivan, Jr. | 600/213 |
| 4,951,690 A | 8/1990 | Baker | |
| 5,007,911 A | 4/1991 | Baker | |
| 5,135,532 A | 8/1992 | Baker | |
| 5,382,250 A | 1/1995 | Kraus | |
| 5,653,712 A | 8/1997 | Stern | |
| 5,658,305 A | 8/1997 | Baker | |
| 5,665,097 A | 9/1997 | Baker et al. | |
| 5,695,338 A | 12/1997 | Robert | |
| 5,711,315 A | 1/1998 | Jerusalmy | |
| 5,775,903 A | 7/1998 | Atkins | |
| 6,102,932 A * | 8/2000 | Kurz | 606/200 |
| 6,238,404 B1 * | 5/2001 | Hidalgo et al. | 606/148 |
| 6,273,720 B1 | 8/2001 | Spalten | |
| 6,382,974 B1 | 5/2002 | Garfinkel | |
| 6,908,469 B2 | 6/2005 | Sellers et al. | |
| 6,997,709 B2 | 2/2006 | Kangasniemi et al. | |
| 7,125,253 B2 | 10/2006 | Kitamura et al. | |
| 7,993,348 B2 * | 8/2011 | Conte et al. | 606/91 |
| 2003/0105469 A1 | 6/2003 | Karmon | |
| 2006/0063973 A1 | 3/2006 | Makower et al. | |
| 2006/0084034 A1 | 4/2006 | Hochman | |
| 2008/0161844 A1 * | 7/2008 | Mossle | 606/171 |
| 2011/0230921 A1 * | 9/2011 | Yamada | 606/86 R |

FOREIGN PATENT DOCUMENTS

| | | |
|---|---|---|
| DE | 3624860 C2 | 10/1994 |
| DE | 389886 C2 | 1/1999 |
| WO | WO89/03198 | 4/1989 |

OTHER PUBLICATIONS

Salvin Dental Specialties Products Catalog, Everything for Your Implant Practice But the Implants, 2006, downloaded Jul. 28, 2008, available at www.salvin.com/Downloads/2006-Salvin-Catalog.pdf.

Introducing the ANKYLOS Implant System, DENTSPLY Friadent CeraMed, 2004.

Sinus Lift Kit, available at www.aceuropa.com/cart.php?target=category&category_id=296, downloaded Mar. 8, 2007.

Bicon Dental Implants, Internal Sinus Lift Technique, available at www.bicon.com/tech/t_SM_ref07.html, downloaded Mar. 8, 2007.

Kitamura, Akira; Drill Device for Sinus Lift; Implant Dentistry; 2005; pp. 340-343; vol. 14(4); Lippincott Williams & Wilkins.

Sotirakis, E: A Different Method for Elevation of the Floor of the Maxillary Sinus: Experimental Study and Reference to Some Cases; Scientific Programme MDIC; 2004.

Codman Craniotomy Kit product description page, Johnson & Johnson Gateway, available at http://www.jnjgateway.com/home.jhtml?loc=CAENG&p.=viewContent&contentld=09008b9880b49, downloaded from Internet on Feb. 5, 2007, as printed on the document.

Our Latest Masterpiece ACRA-CUT SMART DRILL product description (Model 200-500), ACRA-CUT, Inc., 2003.

* cited by examiner

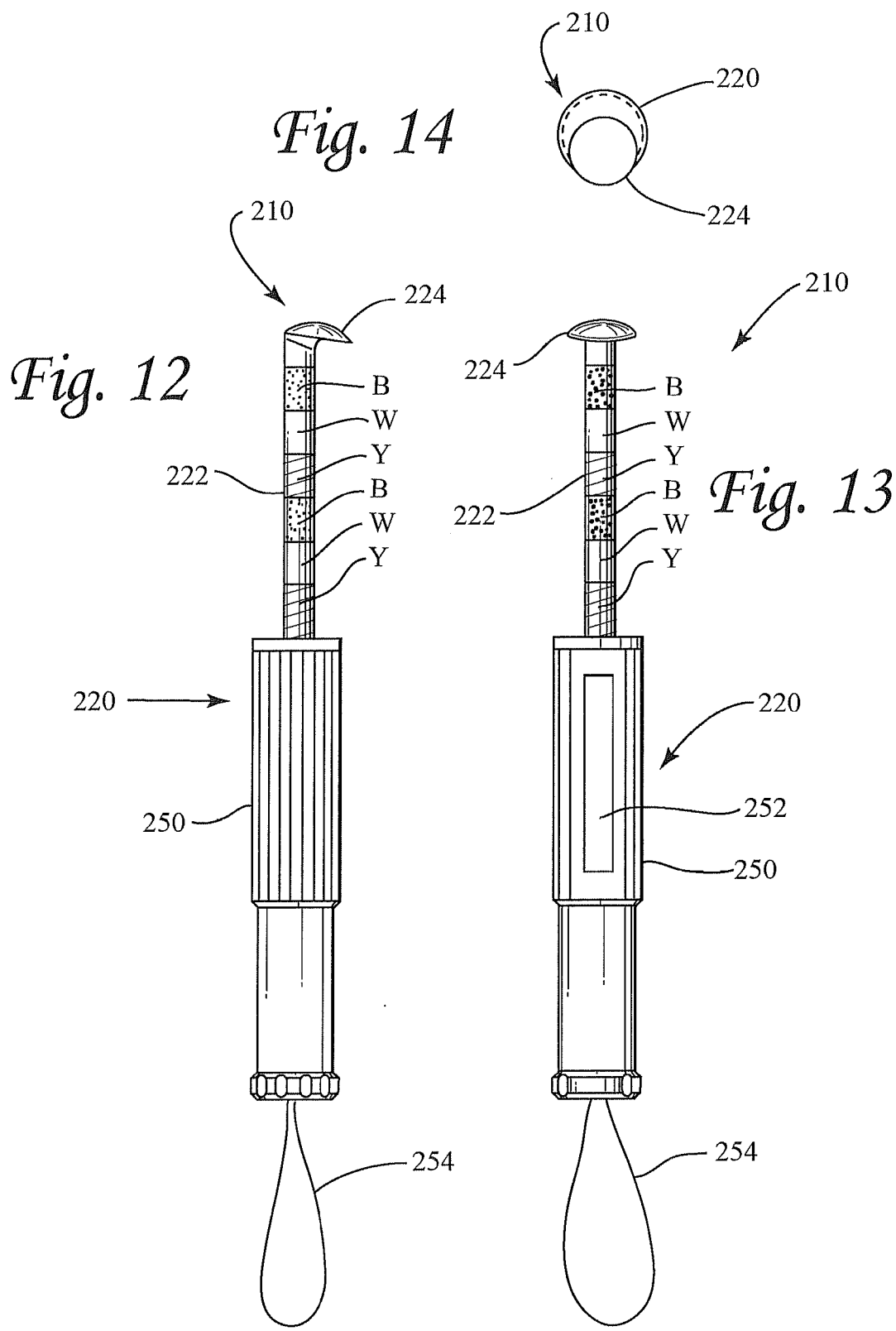

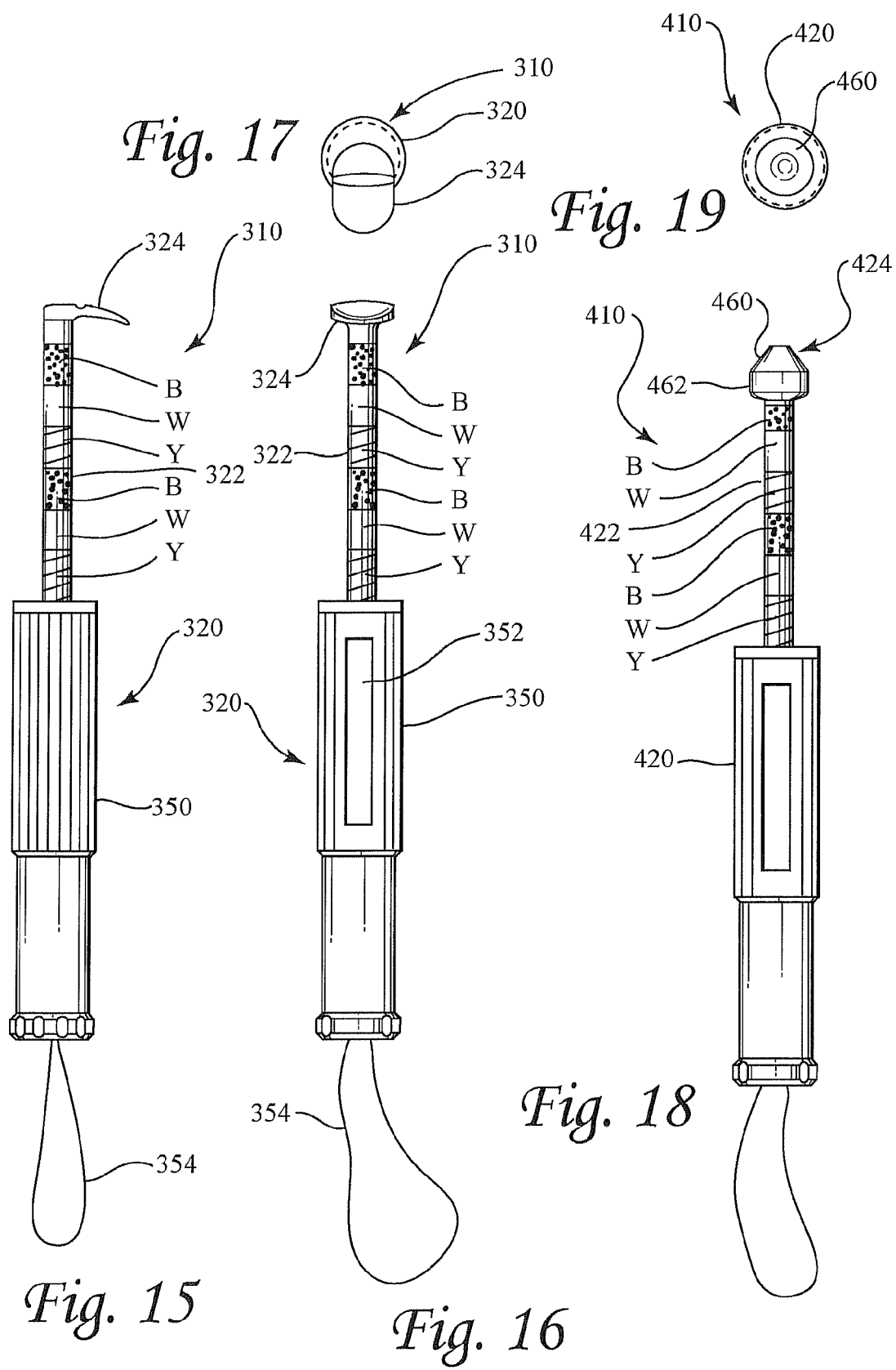

FLEXIBLE TOOLING FOR USE IN MAXILLARY SINUS ELEVATION PROCEDURES AND METHOD OF USING THE SAME

CROSS-REFERENCE TO RELATED APPLICATIONS

This application is a continuation-in-part of International Application No. PCT/US08/52578, filed Jan. 31, 2008, which claims priority from U.S. application Ser. No. 11/669,449, filed Jan. 31, 2007, and is a continuation-in-part of International Application No. PCT/US08/057421 Mar. 19, 2008, which claims priority from U.S. application Ser. No. 11/853,082, filed Sep. 11, 2007, and U.S. Application No. 60/909,240, filed Mar. 30, 2007, all of which are hereby incorporated by reference in their entireties.

BACKGROUND OF THE INVENTION

1. Field of the Invention

This invention relates broadly to dental implants. More particularly, this invention relates to tools for the removal of maxillary bone for access to, dissection of, and elevation of the subantral membrane of the maxillary sinus for osseous regeneration in order to increase the bony support structure for a dental implant, and for receiving a dental implant.

2. State of the Art

Dental implants have been used in dentistry for about 20 years. They offer a tremendous benefit to patients by allowing the replacement of missing teeth. The success of a dental implant is based on a variety of factors including: surgical technique, health of the patient, operator skill and, to a significant part, sufficient bone for the placement and integration of the dental implant. To that end, dental implants are commonly used in the anterior lower jaw, as this region provides sufficient bone quantity, quality and strength to support and hold the dental implant. However, the replacement of the maxillary teeth have presented a considerable challenge because after the loss of maxillary teeth the quality and quantity of the remaining supporting bone may be insufficient to properly and reliably support the dental implant.

More particularly, the maxillary complex is a three-dimensional bone structure composed of alveolar bone and basal bone. The maxillary teeth, and more specifically the teeth roots, are imbedded in the alveolar bone. The top of the maxillary complex forms the floor of the maxillary sinus and is covered by a thin diaphanous membrane known as the subantral or Schneiderian membrane (referred to herein as the "subantral membrane"). Once a tooth is removed from the maxillary complex, the surrounding alveolar bone is frequently resorbed because of the lack of physical stimulation and support of the teeth. This leads to a loss of bone mass and a corresponding reduction in the effective height and thickness of the bone of the maxillary complex, which if not remedied limits the potential use of the dental implant.

To overcome the deficiency of insufficient vertical bone mass of the maxillary complex, several surgical techniques have been developed to increase available bone mass for the placement of dental implants. These techniques augment the bone deficient region with a filler or regenerative material made of natural and/or artificial (synthetic) materials. Such material is placed on the roof of the maxillary structure under the subantral membrane so that it does not interfere with the function of the maxillary sinus. Collectively, these procedures are known within the dental profession as "sinus elevation procedures" with the goal of increasing the vertical height available for placement of dental implants. What makes these techniques unique from other techniques, such as distraction osteogenesis, is that the bone is increased within a body cavity, i.e., the maxillary sinus cavity.

Bone augmentation of the maxillary sinus requires delicate dissection of the subantral membrane from the floor of the sinus. If the membrane is not properly dissected from the bone, bone augmentation may not occur, or may not be sufficient. Unintentional perforation of the subantral membrane may also lead to undesirable short and long-term consequences. If the perforation is large, for example, several millimeters in diameter, the surgeon must either abort the procedure or must use some means of removing or containing the regenerative material on the floor of the sinus to encourage new bone growth. Typically, a collagen membrane patch is used to repair the perforation and contain the regenerative material on the floor of the sinus. A lack of integrity of the membrane can also lead to the migration of regenerative bone materials leading to long-term chronic infections. Therefore, the maintenance of membrane integrity is of utmost importance during the elevation of the membrane to allow placement of regenerative materials with a goal of increasing bone mass in the maxilla.

A commonplace sinus elevation procedure requires a window into the maxillary sinus from a lateral and superior approach to the floor of the sinus. Great care must be taken during the entry to the sinus as it is critical not to perforate the subantral membrane that lines the sinus cavity. Most patients and dental surgeons acknowledge that entrance into the maxillary sinus utilizing a lateral window approach (also known as the Caldwell-Luc procedure) is an invasive procedure. This technique is fraught with many risks and complications because of the limitations of healing potential in the maxillary sinus. In spite of these risks many patients undergo this procedure because of the strong desire to replace missing maxillary teeth with dental implants.

An alternative procedure described by Dr. R. B. Summers approaches the maxillary sinus from the alveolar ridge utilizing solid cylindrical osteotomes. It is a more conservative approach and is less invasive. The technique vertically lifts the subantral membrane from the floor of the maxillary sinus via an infracture of the bony floor. Regenerative material is placed into this space for bone augmentation. The bone regenerative materials are actually used to raise the subantral membrane. The infracture can be performed using solid cylindrical osteotomes with specific diameters that are vertically advanced toward the maxillary sinus producing a mechanical lifting action on the membrane. The technique has a variety of shortcomings as well, including limitations in the ability to carefully dissect (or separate) the subantral membrane from the floor of the sinus. While this technique is safer, an overzealous use of an osteotome during the procedure can result in the perforation of the subantral membrane with disadvantages discussed above.

Several other sinus elevation procedures have also been introduced. One such procedure uses a medical syringe to inject fluid that raises the subantral membrane from the floor of the maxillary sinus. Another technique uses a catheter balloon placed under the subantral membrane in order to raise the subantral membrane from the floor of the maxillary sinus. This procedure requires an infracture of the underlying bone similar to the Summer procedure or a lateral window approach previously described. An additional technique described by Dr. Leon Chen called "Hydraulic Sinus Condensing" drills a small hole in the crest of the alveolar ridge. A steam of water under hydraulic pressure is delivered to the hole, which loosens the sinus membrane. A small window is made on the lateral crest and bone graft material mixed with plasma rich protein is condensed under the loosened sinus membrane. As more and more bone is grafted and condensed, the sinus membrane is elevated. U.S. Patent Application No. 2006/0084034 describes the use of a sleeve that is inserted through the alveolar ridge to the maxillary sinus in order to raise the subantral membrane and form a cavity. In the process, the sleeve can also cut and/or condense bone around itself.

In all of these prior art techniques, tearing or ripping of the subantral membrane may still occur. Such tearing or ripping is also difficult to detect while raising the subantral membrane. Such deficiencies and limitations relate primarily to the inability to carefully separate the membrane from its physical adherence to the floor of the maxillary sinus. Overcoming these previous limitations in the technique of sinus elevation will reduce infection, bleeding, swelling, pain, suffering and failure when using dental implants in the maxillary sinus.

SUMMARY OF THE INVENTION

The present invention provides tooling and methodologies for separating and dissecting the subantral membrane from the floor of the maxillary sinus, as well as for implanting bone, bone substitute, and/or an osseogenesic material under the dissected and elevated subantral membrane.

The tooling for dissecting employ thin member extending from the distal end of a support structure. The thin member has a first peripheral region disposed opposite a second peripheral region. The first peripheral region is joined to or integrally formed with the distal end of the support structure. The second peripheral region defines a thin blade-like section for dissecting the subantral membrane from the floor of the maxillary sinus.

In the preferred embodiment, the blade-like section is angled downward away from the distal support structure, which aids in positioning the blade-like section on the floor of the maxillary sinus during use.

In the illustrative embodiment, the thin member extending from the distal end of the support structure has a convex top surface, and the thin member is generally circular or oblong in shape. The thin member can also be deformable such that it bends downward and upward relative to the support structure adjacent thereto. The support structure adjacent the thin member can have colored markings at regular intervals along its length to aid in depth positioning. The support structure may be rotatably coupled to a handle to allow rotation of the thin member relative to the handle.

An additional tool for implanting and packing bone regenerative material under the dissected and elevated sinus membrane includes a manually grippable support structure and a head portion mounted thereon. The head portion is bendable about a groove defining a living hinge and includes a stop which limits bending of the head portion during bone compaction. If a portion of the head is caught on the maxillary bone during withdrawal of the tool, then the head can bend along the hinge to facilitate tool withdrawal.

The tooling can be packaged as a kit that includes a plurality of hand-held devices as described above, with one of the devices having a thin member with a first maximal dimension, and another one of the devices having a thin member with a second maximal dimension, the first maximal dimension being smaller than the second maximal dimension. In addition, the bone packing tool can also be provided as part of the kit.

The tooling described herein can be used to dissect and elevate the subantral membrane by methodology that inserts the thin member and portions of the support structure of the tooling into a hole leading from below through the anterior maxilla bone to the bottom side of the maxillary sinus. The tooling is manually manipulated such that thin member of the tooling elevates and dissects the subantral membrane from the floor of the maxillary sinus thereby creating a space therebetween. Bone regenerative material is packed into this space, where it hardens and bonds to the surrounding bone of the anterior maxilla in order to increase the bone mass of the anterior maxilla and support a dental prosthesis that is implanted therein.

Advantageously, the tooling is insertable through a hole leading from below through the anterior maxilla bone to the bottom side of the maxillary sinus, and is operated to elevate and dissect the subantral membrane via access through such hole. In this manner, a window from a lateral and superior approach to the floor of the sinus is avoided along with the risks and complications that are associated therewith. Moreover, the thin blade-like section of the distal member of the tooling can be used to efficiently and effectively dissect the subantral membrane from the floor of the maxillary sinus, while reducing the risk of tearing or ripping the subantral membrane.

Additional features and advantages of the invention will become apparent to those skilled in the art upon reference to the detailed description taken in conjunction with the provided figures.

BRIEF DESCRIPTION OF THE DRAWINGS

FIG. 12 is a side elevation of a third exemplary tool for elevating and dissecting the subantral membrane in accordance with the present invention.

FIG. 13 is a front elevation of a the tool of FIG. 12.

FIG. 14 is a top view of the tool as shown in FIG. 13.

FIG. 15 is a side elevation of a fourth exemplary tool for elevating and dissecting the subantral membrane in accordance with the present invention.

FIG. 16 is a front elevation of the tool of FIG. 15.

FIG. 17 is a top view of the tool as shown in FIG. 16.

FIG. 18 is a side elevation of a tool for packing bone under the elevating and dissected subantral membrane in accordance with the present invention.

FIG. 19 is a top view of the tool shown in FIG. 18.

DETAILED DESCRIPTION

As used herein, the term "distal" is generally defined as in the direction away from a user of the system/apparatus/device. Conversely, "proximal" generally means in the direction toward the user of the system/apparatus/device.

Turning now to FIGS. 1-5, there is shown a first embodiment of a tool 10 for dissection and elevation of the subantral membrane in accordance with the present invention. The tool 10 includes an elongate handle 12 preferably with knurled exterior surfaces (not shown) for efficient gripping. The handle 12 can also have a tapered distal end 14 as shown. The handle 12 is preferably on the order of 100 mm to 110 mm in length with an outer diameter on the order of 6.0 mm.

A first extension arm 16 projects from the distal end 14 of the handle 12 in a manner coaxial to the central axis of the handle 12. In the preferred embodiment, the first extension arm 16 is rigidly coupled to (or possibly integrally formed with) the handle 12 such that it does not rotate or translate relative to the handle 12. The first extension arm 16 is preferably on the order of 10 mm to 40 mm in length (more preferably on the order of 30 mm as shown) with an outer diameter on the order of 3 mm.

Figure 1:
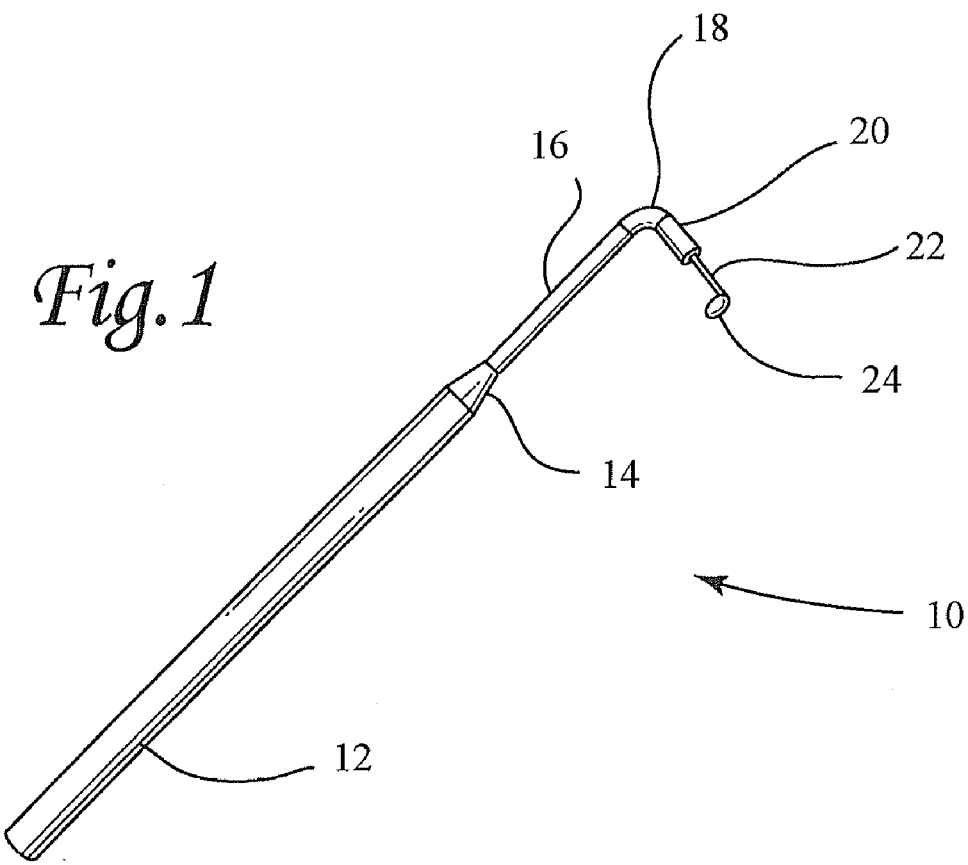
FIG. 1 is a perspective view of a first exemplary tool for elevating and dissecting the subantral membrane in accordance with the present invention.
Figure 2:
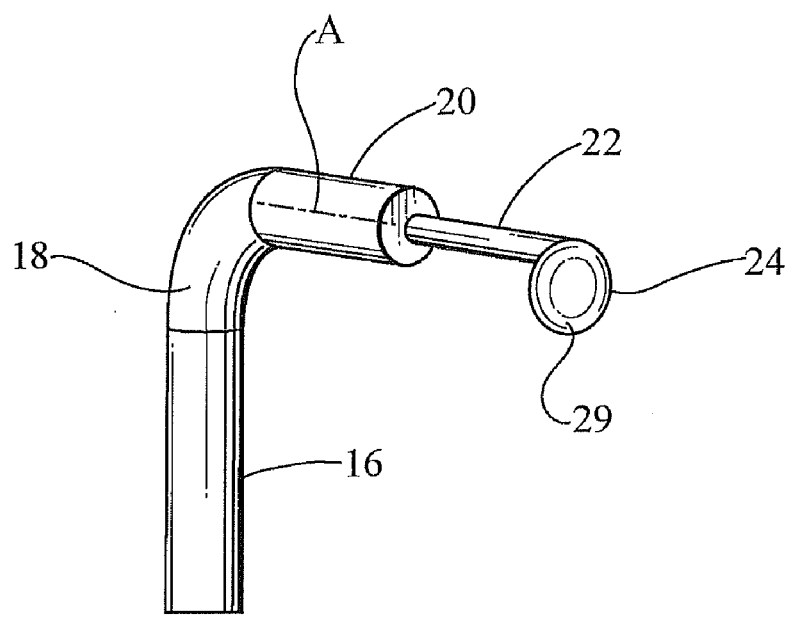
FIG. 2 is a perspective view of a distal portion of the exemplary tool of FIG. 1.

An elbow 18 extends from the distal end of the first extension arm 16 to a second extension arm 20. Preferably the elbow 18 provides a 90-degree turn such that the second extension arm 20 is substantially orthogonal relative to the first extension arm 16 and handle 12. The second extension arm 20 is preferably rotatably coupled relative to the elbow 18 to allow axial rotation of the second extension arm 20; i.e., about longitudinal axis A (FIG. 2). Such rotatable coupling can include, e.g., a snap fit at the elbow or a sleeve the extends over a hub projecting from the elbow and which is then swaged or crimped in place. Alternatively, the second extension arm 20 can be rigidly coupled to the elbow 18 such that it does not rotate relative to the elbow 18. The second extension arm 20 can be provided with knurled exterior surfaces (not shown) for efficient manipulation. The elbow 18 and the second extension arm 20 preferably have an outer diameter that corresponds to the outer diameter on the order of 3 mm. The second extension arm 20 is preferably on the order of 5 mm to 30 mm in length (more preferably on the order of 10 mm as shown). The handle 12, first extension arm 16, elbow 18, and second extension arm 20 can all formed together from a medical grade plastic material such as polycarbonate or ABS. Alternatively, the components may be formed separately and coupled together from like or different materials. For example, the second extension arm 20 can be made from stainless steel.

A mandrel 22 extends from the distal end of the second extension arm 20 preferably in a manner that is coaxial with the central axis of the arm 20. In the preferred embodiment, the mandrel 22 is rigidly coupled to (or possibly integrally formed with) the second extension arm 20 such that it does not rotate or translate relative to the second extension arm 20. The mandrel 22 is preferably on the order of 10 mm to 15 mm in length (more preferably on the order of 12 mm in length as shown) with an outer diameter on the order of 0.8 to 1.0 mm. The exterior surface of the mandrel 22 can have color markings at fixed intervals along its length to aid in depth positioning. For example, in the embodiment shown in FIG. 5, the mandrel 22 is 30 mm in length with color markings realized by a sequence of six sections that are colored yellow (Y), blue (B), white (W), yellow (Y), blue (B), white (W) as shown. Each colored section is preferably 5 mm in length. The mandrel 22 is preferably substantially rigid and does not bend in response to loads applied thereto during its intended use.

Figure 3:
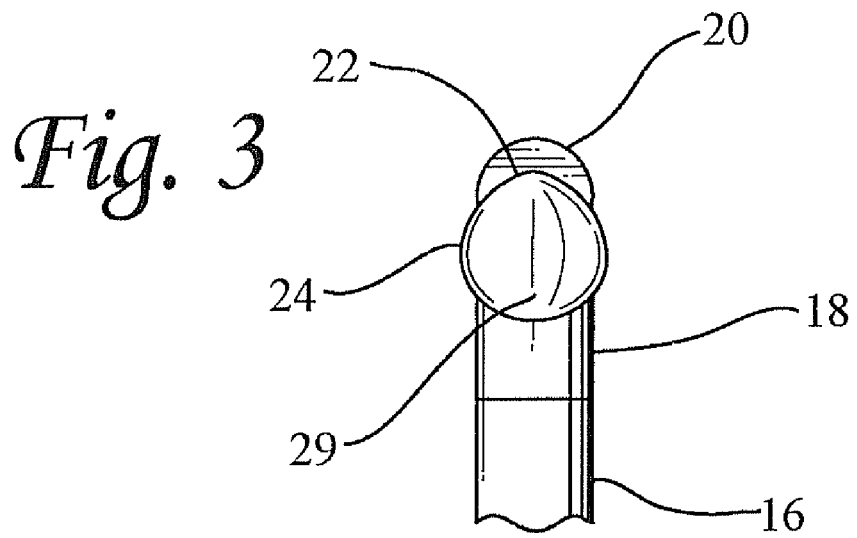
FIG. 3 is a front schematic view of a distal portion of the exemplary tool of FIG. 1.
Figure 4:
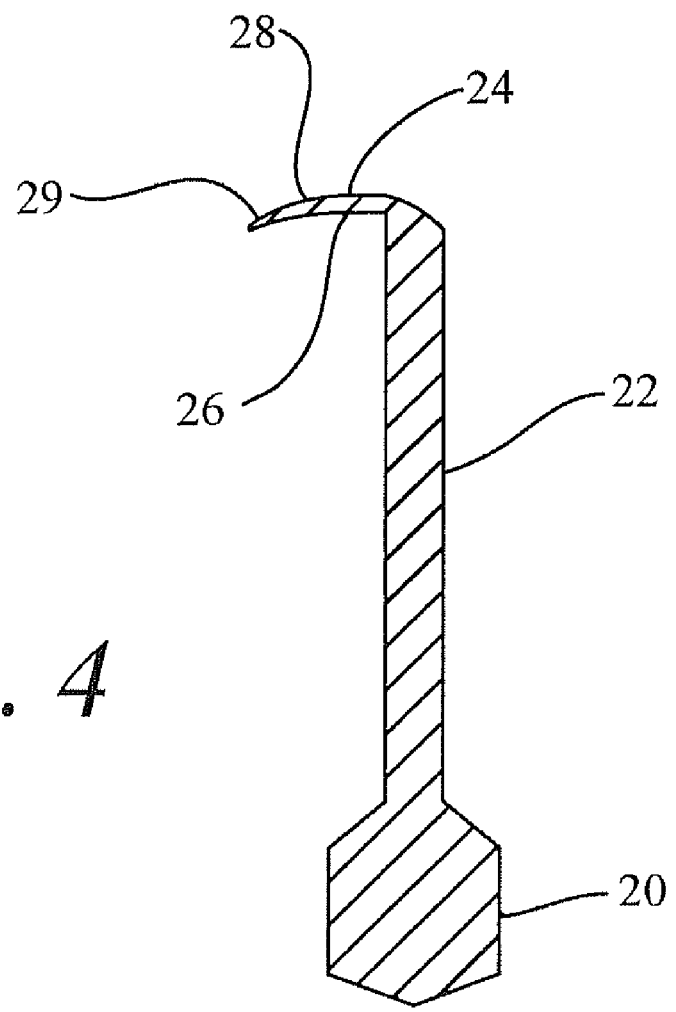
FIG. 4 is a cross-sectional view of a distal portion of the exemplary tool of FIG. 1.

A member 24 extends from the distal end of the mandrel 22 preferably at a direction that is substantially orthogonal relative to the central axes of the mandrel 22 and the second extension arm 20 and substantially parallel to the first extension arm 16 and handle 12, as best shown in FIG. 2. The member 24 is preferably elastomeric with a thickness preferably between 0.15 mm and 0.50 mm (most preferably on the order of 0.25 mm). The member 24 preferably has a concave or flat bottom surface 26 and has a convex top surface 28 directed away from the mandrel 22. The bottom surface 26, when concave, preferably has a radius of curvature on the order of 4.3 mm, and the convex top surface 28 preferably has a radius of curvature on the order of 3.1 mm. The member 24 has a generally circular shape as best shown in FIG. 3 with a diameter on the order of 2.5 mm to 8.0 mm (most preferably 3.75 mm as shown). The member 24 is rigidly joined to (or integrally formed with) the mandrel 22 at or near the periphery of the member 24 such that central axis of the mandrel 22 is offset from the central region of the member 24 as best shown in FIG. 4. The periphery of the member 24 that is disposed opposite the mandrel 22 defines a flexible, thin and curved blade-like section 29 that is preferably angled downward away from the mandrel 22 (as best shown in FIG. 4) and generally toward the first extension arm 16 of the handle 12. The thin blade-like section 29 is used to dissect the subantral membrane from the floor of the maxillary sinus as described below in greater detail. The edge of the blade-like section 29 is offset from the mandrel 22 at a maximum distance corresponding to the maximal dimension of the member 24. This distance dictates the lateral reach of the blade-like section 29 along the floor of the maxillary sinus during the dissection process. The downward angle of the blade-like section 29 allows the user to locate and maintain the blade-like section 29 in contact with the floor of the maxillary sinus during the dissection process, which aids in minimizing the risk of perforating the subantral membrane during the dissection process. The member 24 is preferably realized from a polymeric material, e.g., a copolyester thermoplastic elastomer such as sold by Ticona under the Riteflex tradename, and preferably has a shore hardness d scale value of preferably between approximately 30 and 50 and more preferably 40±5.

Figure 5A:
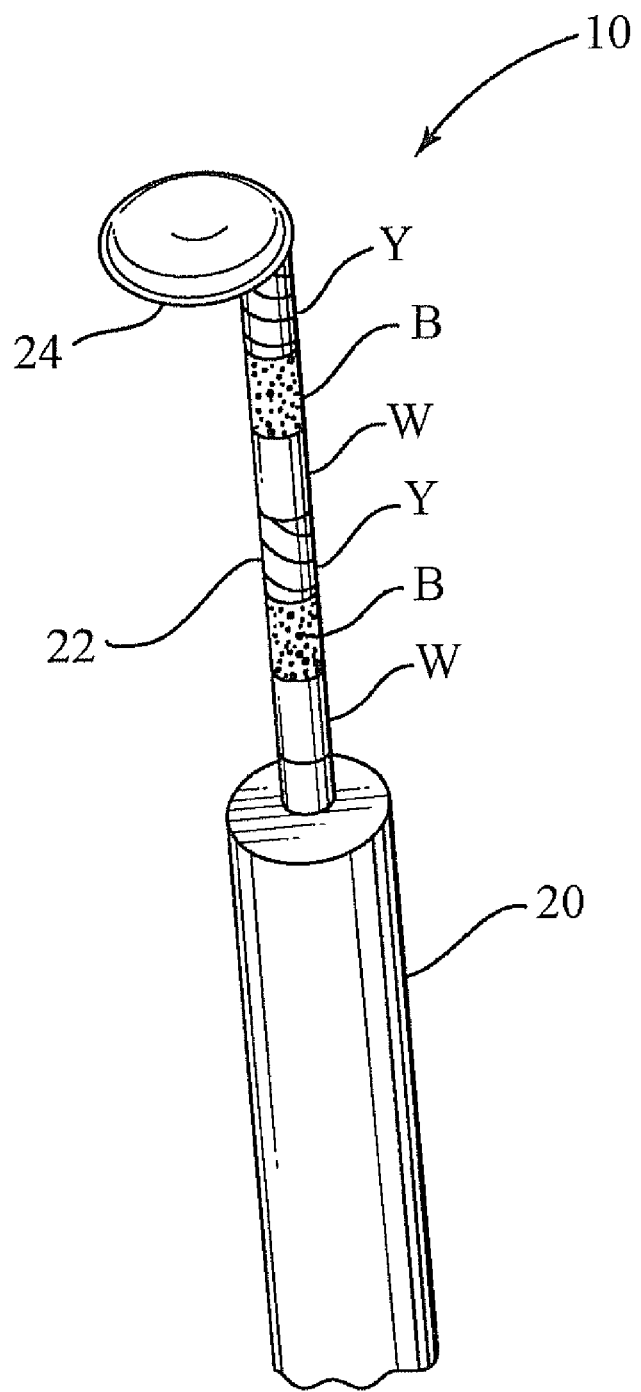
FIG. 5A is a schematic illustration of a distal portion of the exemplary tool of FIGS. 1-4.
Figure 5B:
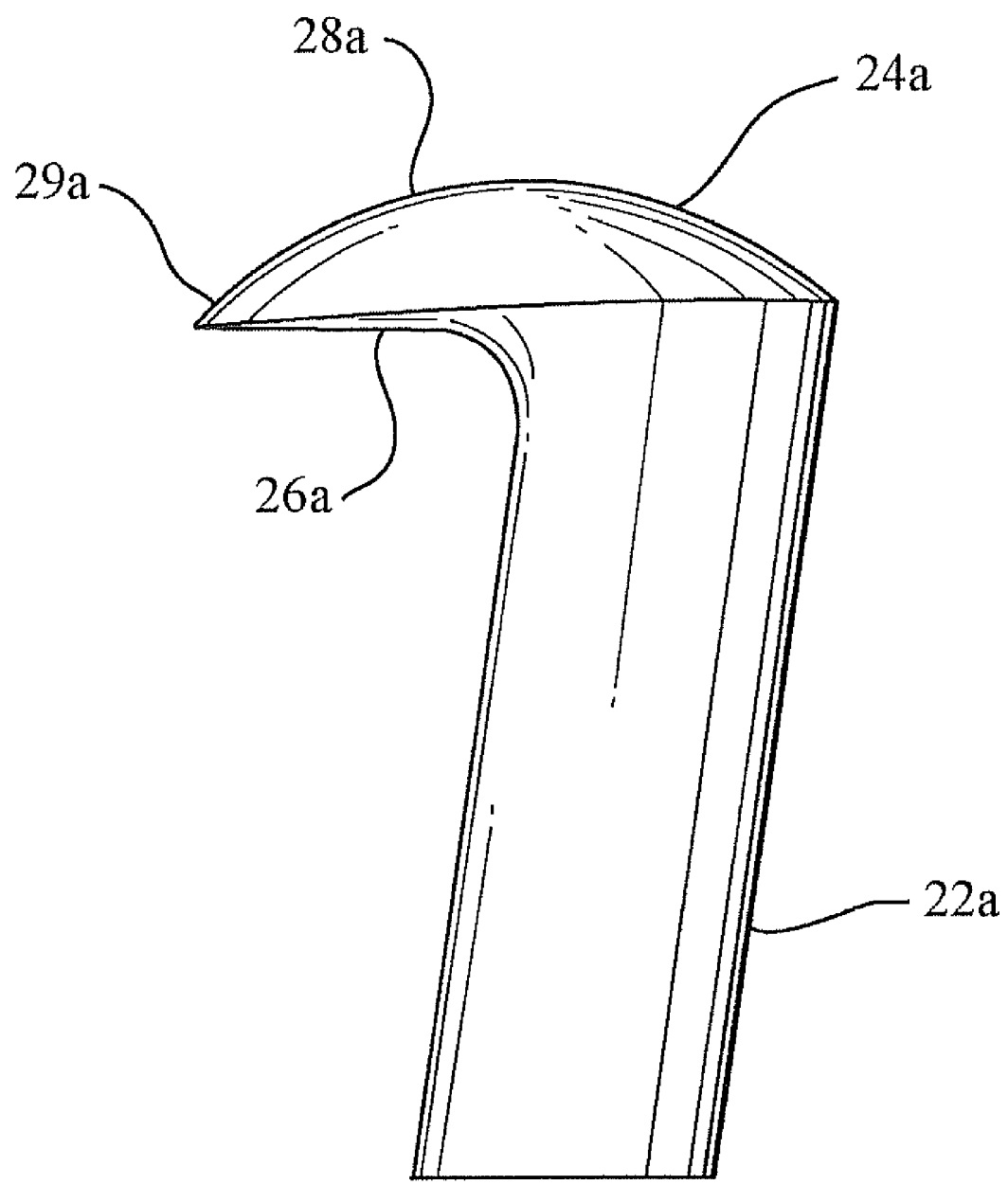
FIG. 5B is an enlarged side elevation of another embodiment of an elastomeric member of the exemplary tool of FIGS. 1-5A.
Figure 6:
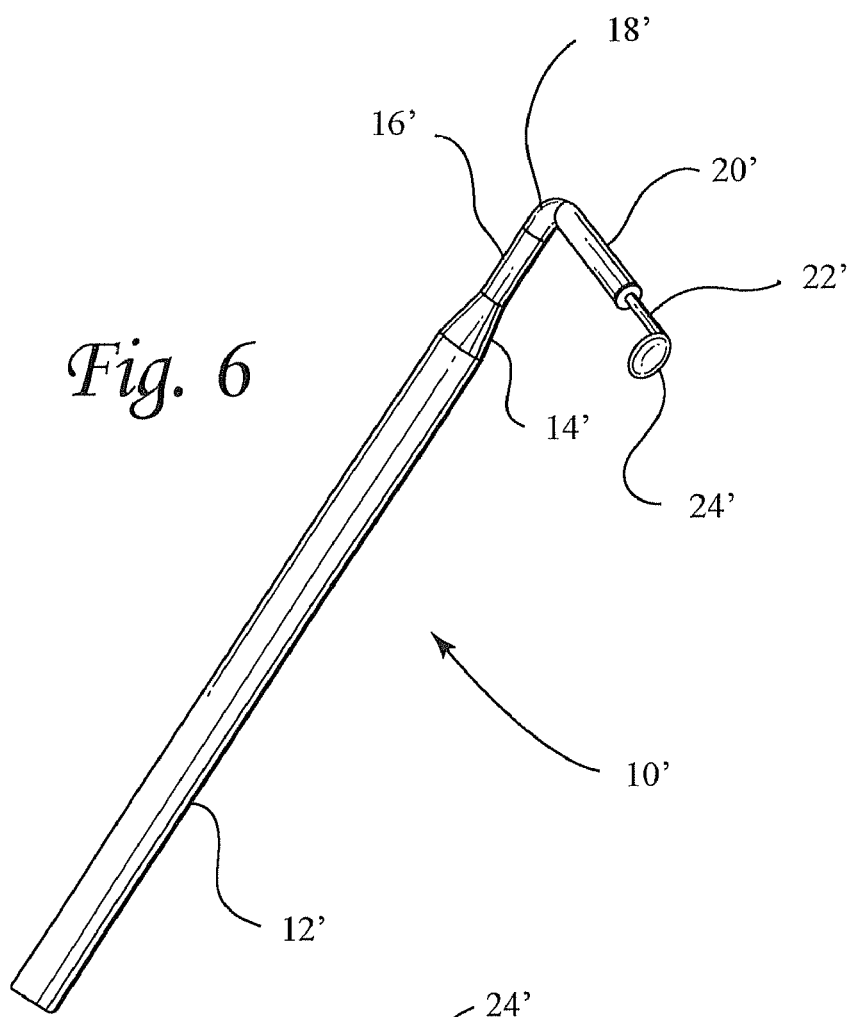
FIG. 6 is a perspective view of a second exemplary tool for elevating and dissecting the subantral membrane in accordance with the present invention

Referring to FIG. 5B, another embodiment for a member 24a at the distal end of the mandrel 22a is shown. Member 24a is preferably made from the same material as member 24, and has a lower surface 26a, a convex upper surface 28a, and an acutely angled blade-like section 29a. Member 24a is thicker than member 24, providing a more bulbous overall design. However, the blade preferably has a leading angle of less than 40°, and the lower surface is preferably concave or otherwise configured to direct the blade-like section 29a slightly downward. These features facilitate dissection of the subantral membrane from the floor of the maxillary sinus, yet provide a rounded contacting surface (28a) that will not puncture the membrane.

In the preferred embodiment, the member 24 and mandrel 22 are formed by insert molding wherein the outer sleeve of the mandrel 22 and the member 24 are realized from a thermoplastic material molded around the inner core of the mandrel 22. The member 24 may also be attached to the mandrel via other mechanisms, including bonding, swaging, threading, press fitting, and riveting.

Turning now to FIGS. 6-10, there is shown a second embodiment of a tool 10' for dissection and elevation of the subantral membrane in accordance with the present invention. The tool 10' includes an elongate handle 12' preferably with knurled exterior surfaces (not shown) for efficient gripping. The handle 12' can also have a tapered distal end 14' as shown. The handle 12' is preferably on the order of 100 mm to 110 mm in length with an outer diameter on the order of 6 mm.

A first extension arm 16' projects from the distal end 14' of the handle 12' in a manner that is coaxial with the central axis of the handle 12'. In the preferred embodiment, the first extension arm 16' is rigidly coupled to (or possibly integrally formed with) the handle 12' such that it does not rotate or translate relative to the handle 12'. The first extension arm 16' is preferably on the order of 10 mm to 40 mm in length (more preferably on the order of 30 mm as shown) with an outer diameter on the order of 3 mm.

An elbow 18' extends from the distal end of the first extension arm 16' to a second extension arm 20'. Preferably the elbow 18' provides a 90-degree turn such that the second extension arm 20' is substantially orthogonal relative to the first extension arm 16' and handle 12'. The second extension arm 20' is preferably rotatably coupled relative to the elbow 18' to allow axial rotation of the second extension arm 20'. Such rotatable coupling can include, e.g., a snap fit at the elbow or a sleeve the extends over a hub projecting from the elbow and which is then swaged or crimped in place. Alternatively, the second extension arm 20' can be rigidly coupled to the elbow 18' such that it does not rotate relative to the elbow 18'. The second extension arm 20' can be provided with knurled exterior surfaces (not shown) for efficient manipulation. The elbow 18' and the second extension arm 20' preferably have an outer diameter that corresponds to the outer diameter on the order of 3 mm.

The elbow 18' and the second extension arm 20' preferably have an outer diameter on the order of 3 mm. The second extension arm 20' is preferably on the order of 5 mm to 30 mm in length (more preferably on the order of 10 mm as shown).

The handle 12', first arm extension 16', elbow 18', and second arm extension 20' of tool 10' can be constructed and assembled in the same manner as the corresponding elements of tool 10.

A mandrel 22' extends from the distal end of the second extension arm 20' preferably in a manner that is coaxial with the central axis of the arm 20'. In the preferred embodiment, the mandrel 22' is rigidly coupled to (or possibly integrally formed with) the second extension arm 20' such that it does not rotate or translate relative to the second extension arm 20'.

The mandrel 22' is preferably on the order of 10 mm to 15 mm in length (more preferably on the order of 12 mm in length as shown) with an outer diameter on the order of 0.8 to 1.0 mm. The exterior surface of the mandrel 22' can have color markings at fixed intervals along its length to aid in depth positioning. For example, in the embodiment shown in FIG. 10A, the mandrel 22' is 30 mm in length with color markings realized by a sequence of six sections that are colored yellow (Y), blue (B), white (W), yellow (Y), blue (B), white (W) as shown. Each colored section is 5 mm in length. The mandrel 22' is preferably substantially rigid and does not bend in response to loads applied thereto during its intended use.

Figure 7:
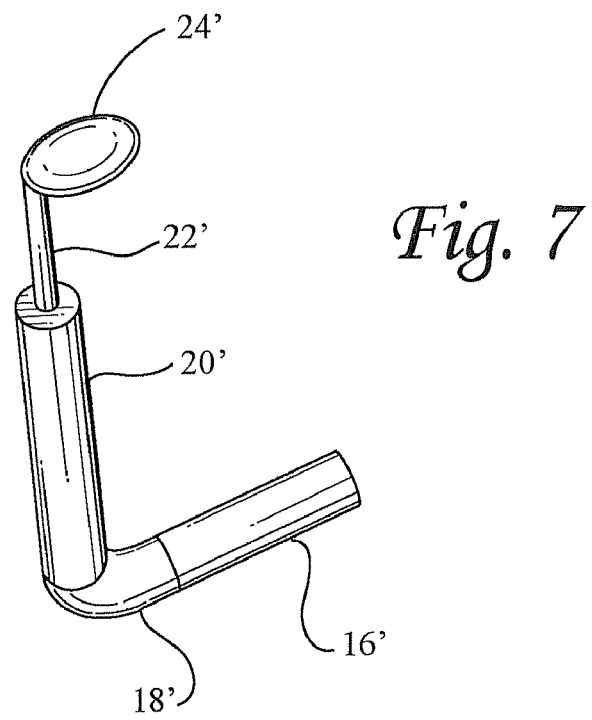
FIG. 7 is a perspective view of a distal portion of the exemplary tool of FIG. 6.
Figure 8:
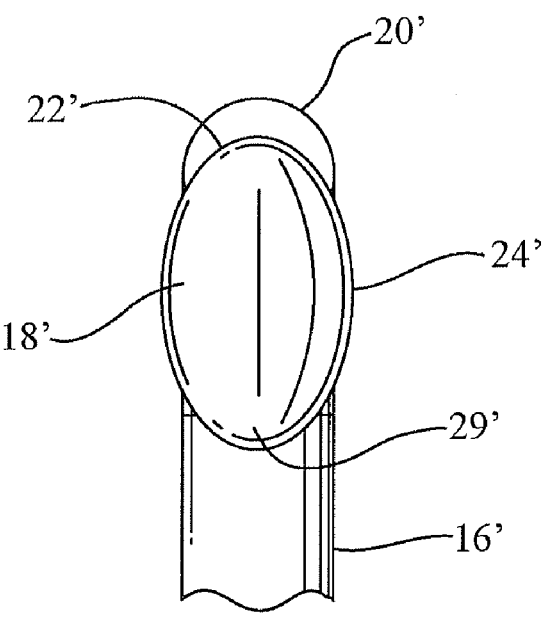
FIG. 8 is a front schematic view of a distal portion of the exemplary tool of FIG. 6.
Figure 9:
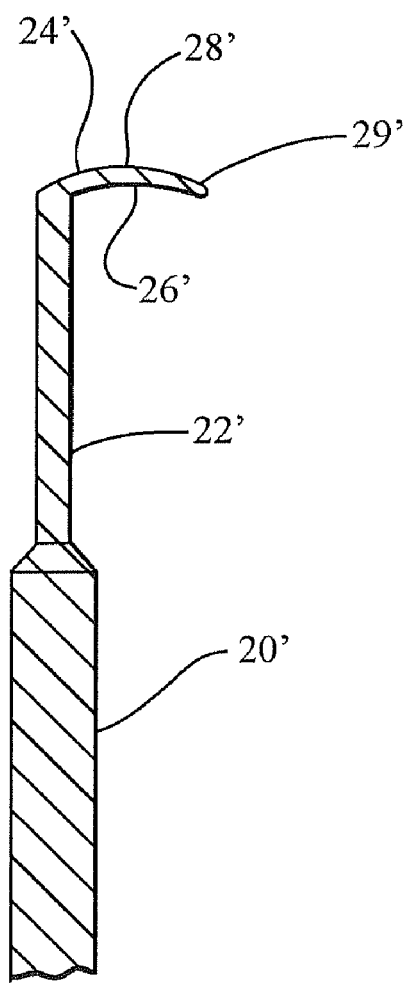
FIG. 9 is a cross-sectional view of a distal portion of the exemplary tool of FIG. 6.

A member 24' extends from the distal end of the mandrel 22' preferably at a direction that is proximally and substantially orthogonal relative to the central axis of the mandrel 22' and second extension arm 20' (and thus parallel to the first extension arm 16' and handle 12') as best shown in FIG. 7. The member 24' is thin with a thickness preferably between 0.15 mm and 0.50 mm (most preferably on the order of 0.25 mm). The member 24' has a concave bottom surface 26' and a convex top surface 28' directed away from the mandrel 22'. The concave bottom surface 26' preferably has a radius of curvature on the order of 4.3 mm, and the convex top surface 28' preferably has a radius of curvature on the order of 3.1 mm. The member 24' has a generally oblong, and preferably oval, shape as best shown in FIG. 8 with a maximal diameter on the order of 2.5 mm to 8.0 mm (most preferably 6.0 mm as shown). The member 24' is rigidly joined to (or integrally formed with) the mandrel 22' at or near the periphery of the member 24' such that central axis of the mandrel 22' is offset from the central region of the member 24' as best shown in FIG. 9. The periphery of the member 24' that is disposed opposite the mandrel 22' defines a thin, flexible and curved blade-like section 29' that is angled downward away from the mandrel 22' (as best shown in FIG. 9) and generally toward the first extension arm 16' of the handle 12'. The thin blade-like section 29' is used to dissect the subantral membrane from the floor of the maxillary sinus as described below in greater detail. Member 24' is coupled to the mandrel 22' at a periphery of member 24' such that the edge of the blade-like section 29' is offset from the mandrel 22' at a maximum distance substantially corresponding to the maximal dimension of the member 24'. This distance dictates the lateral reach of the blade-like section 29' along the floor of the maxillary sinus during the dissection process. The downward angle of the blade-like section 29' allows the user to locate and maintain the blade-like section 29' in contact with the floor of the maxillary sinus during the dissection process, which aids in minimizing the risk of perforating the subantral membrane during the dissection process.

The member 24' is preferably realized from a polymeric material, e.g., a copolyester thermoplastic elastomer such as sold by Ticona under the Riteflex tradename, and preferably has a shore hardness d scale value of preferably between approximately 30 and 50 and more preferably 40±5.

The member 24' is also preferably flexible such that it can deform and bend up and down for insertion and removal from a hole through the anterior maxilla as described below in more detail. In the preferred embodiment, the member 24' and mandrel 22' are formed by insert molding wherein the outer sleeve of the mandrel 22' and the member 24' are realized from a thermoplastic material molded around the inner core of the mandrel 22'. The member 24' may be coupled to the mandrel 22' in any of the ways member 24 is coupled to mandrel 22.

Figure 10A:
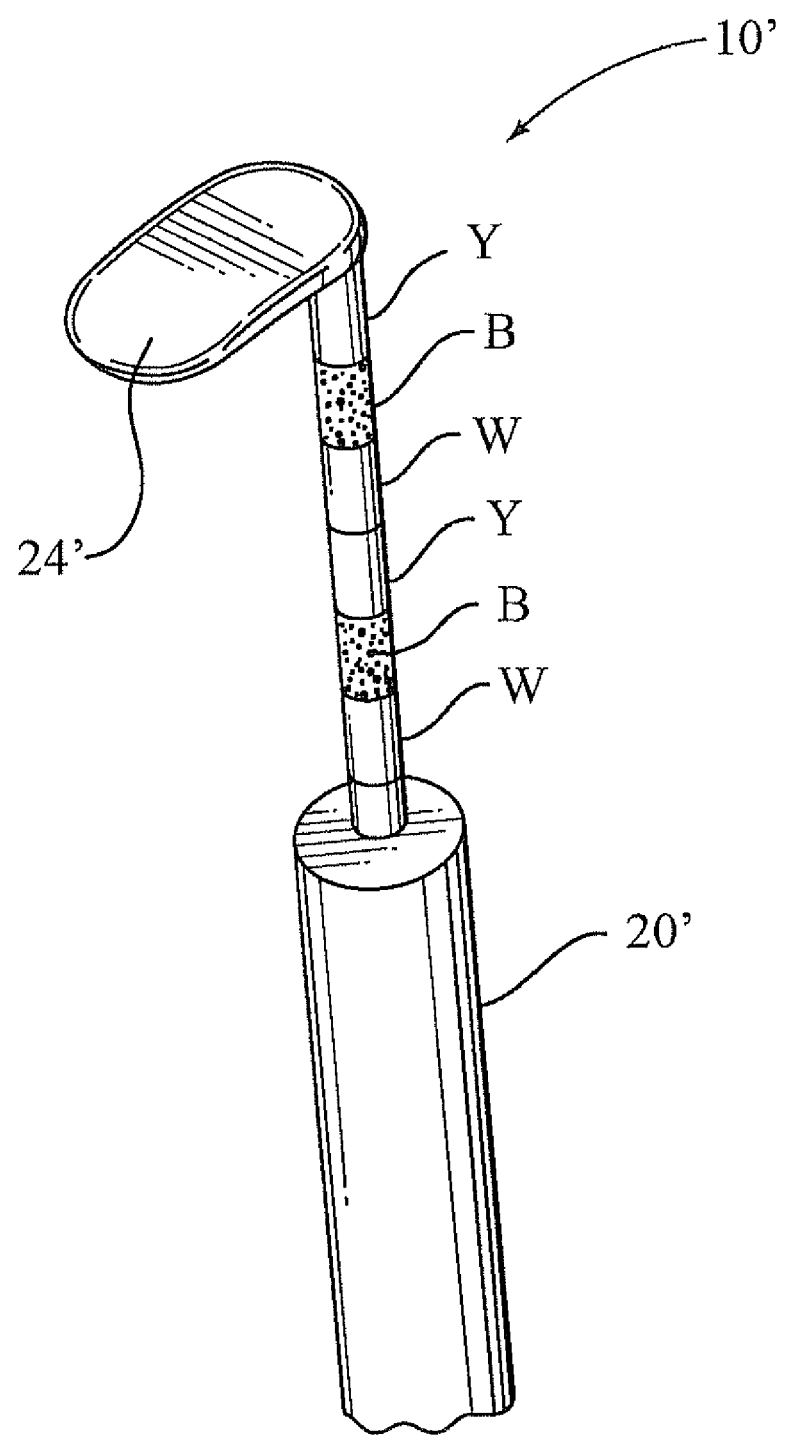
FIG. 10A is a schematic illustration of a distal portion of the exemplary tool of FIGS. 6-9.
Figure 10B:
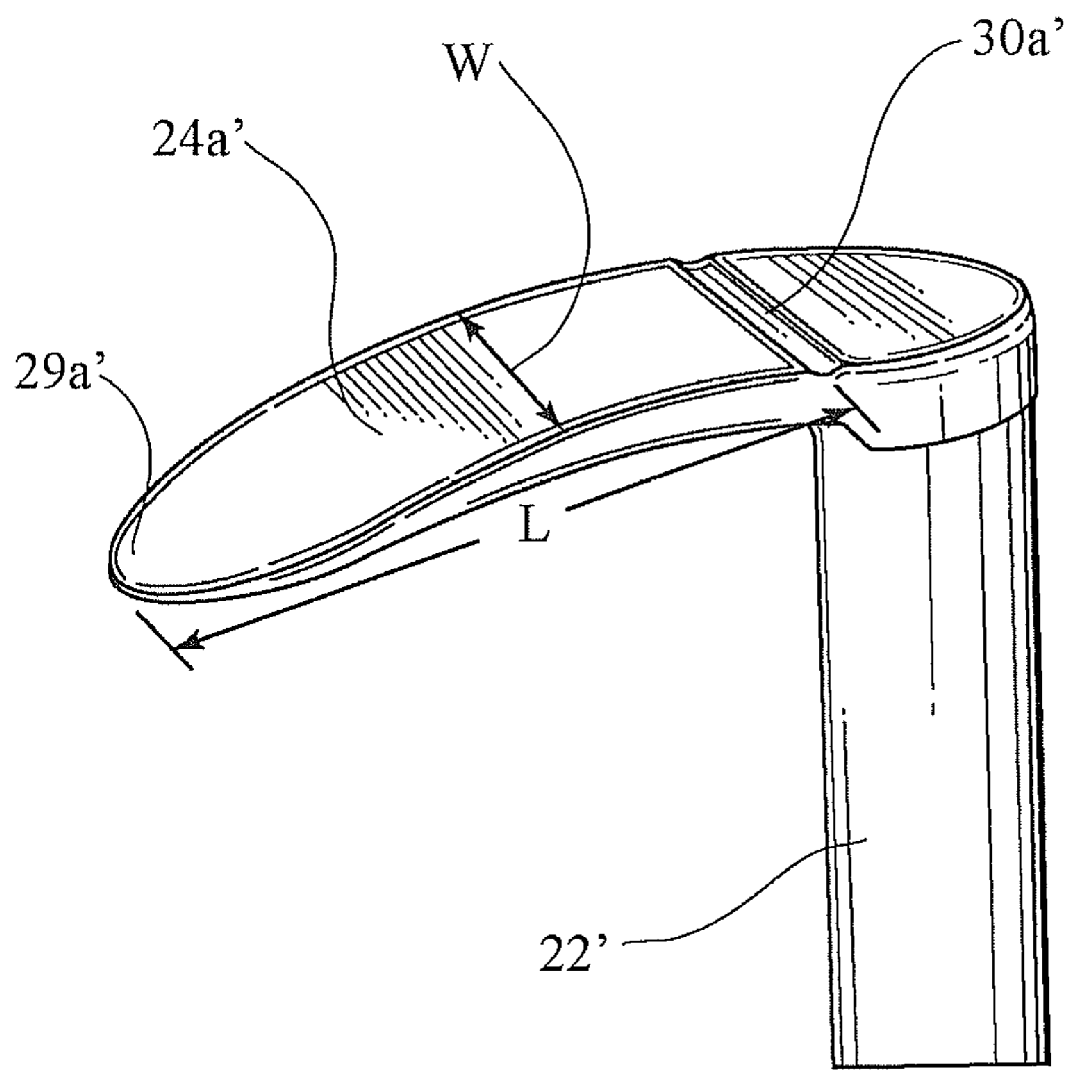
FIG. 10B is an enlarged perspective view of another embodiment of an elastomeric member of the exemplary tool of FIGS. 6-10A.

Referring to FIG. 10B another embodiment of a member 24a' provided at the distal end of the mandrel 22' is shown. The member 24a' is substantially similar to member 24', but includes groove 30a' to aid in flexing for insertion through the hole in the anterior maxilla. The member 24a' is relatively narrow, having a length L to width W ratio of approximately 4.5 from groove 30a' to the end of the blade 29a'. The blade also tapers in thickness from the groove 30a' to its end, and has a curved top profile, designed to facilitate entry between the subantral membrane and the floor of the sinus cavity.

The tooling described herein are preferably used for dissection and elevation of the subantral membrane in accordance with the present invention as exemplified in FIGS. 11A to 11K. Note that the tool 10 of the first embodiment is referred to below as the first tool and the tool 10' of the second embodiment is referred to as the second tool, with the second tool 10' having a larger flexible member than the flexible member of the first tool 10. The tooling can be packaged as a kit that includes both the first tool and the second tool. Similar tool(s) with different sizes and shapes or other features can also be included in the kit.

Figure 11A:
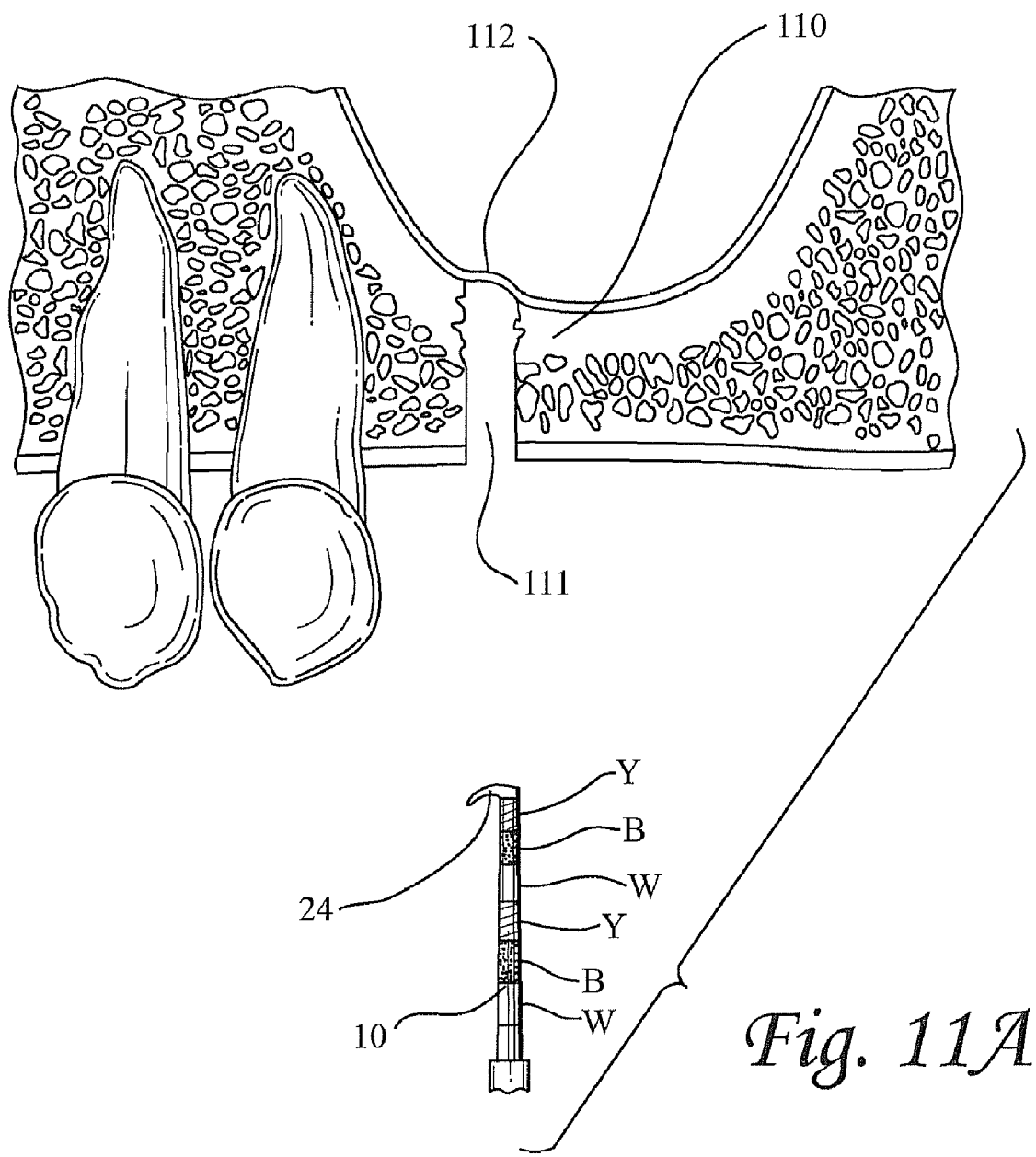
FIGS. 11A-11K are schematic illustrations of an exemplary methodology that uses the tooling of FIGS. 1-10B to elevate and dissect the subantral membrane from the floor of the maxillary sinus.

The methodology begins with the user forming a hole 111 into the anterior maxilla 110 from below as illustrated in FIG. 11A. The center of the hole 111 is positioned at or near the desired central axis of the implant. The hole 111 extends through the anterior maxilla to expose the bottom side of the maxillary sinus membrane 112 as shown. The hole 111 preferably has a diameter that is slightly larger than the characteristic dimension of the flexible member 24 of the first tool and that is smaller than the characteristic dimension of the flexible member 24' of the second tool 10', for example on the order of 4.0 mm.

The user then manually manipulates the first tool 10 such that the flexible member 24 and mandrel 22 of the first tool 10 are inserted through the hole 111 and advanced upward such that the member 24 contacts the bottom side of the subantral membrane 112. The color markings on the mandrel 22 can be used to aid in depth positioning of the first tool 10.

Figure 11B:
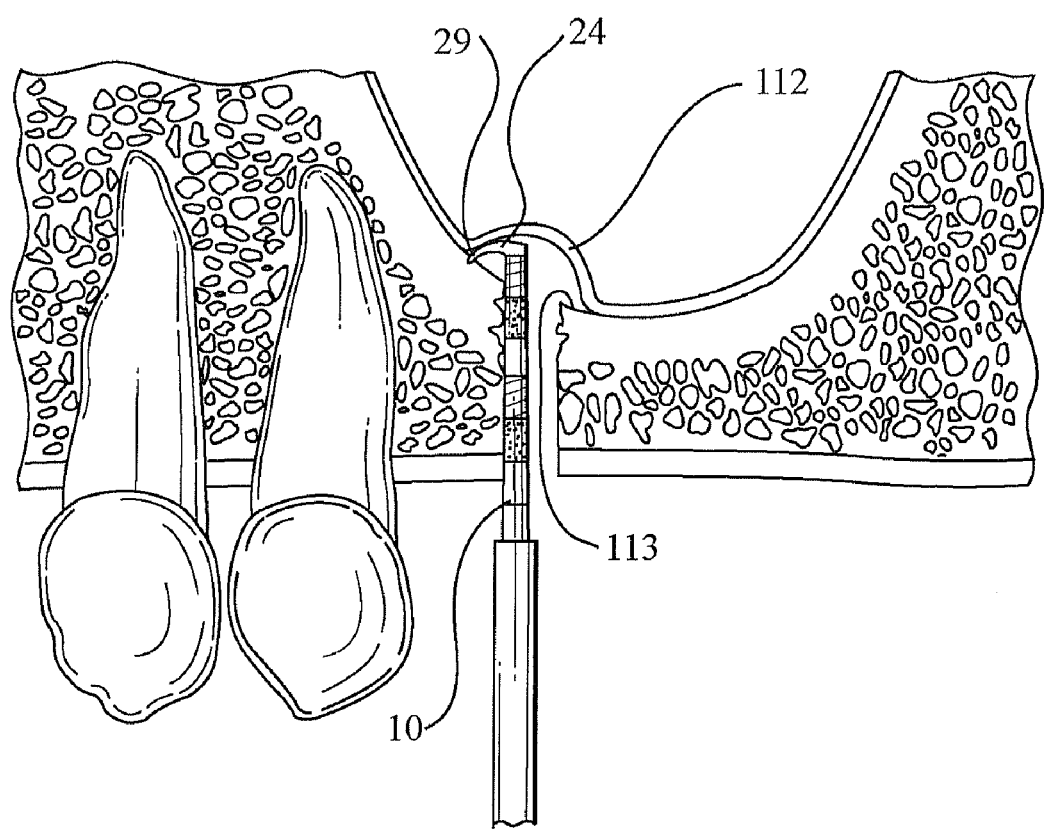

The user then manually manipulates the handle 12 (and/or possible other part(s) of the tool 10) to apply forces that push the member 24 upward, which causes initial separation of the subantral membrane 112 from the floor of the maxillary sinus. Such separation creates a small space between the subantral membrane and the floor 113 of the maxillary sinus. The user then manually manipulates the handle 12 (and/or possible other part(s) of the tool 10) to position the thin blade-like section 29 of the member 24 on the floor of the maxillary sinus and to subsequently move the member 24 laterally back and forth in small strokes such that the blade-like section 29 pushes against the subantral membrane and dissects the membrane from the floor of the maxillary sinus in the region outside but near the hole as shown in FIG. 11B. These strokes can be continued to effectuate membrane separation at distances further and further from the edge of the hole.

Figure 11C:
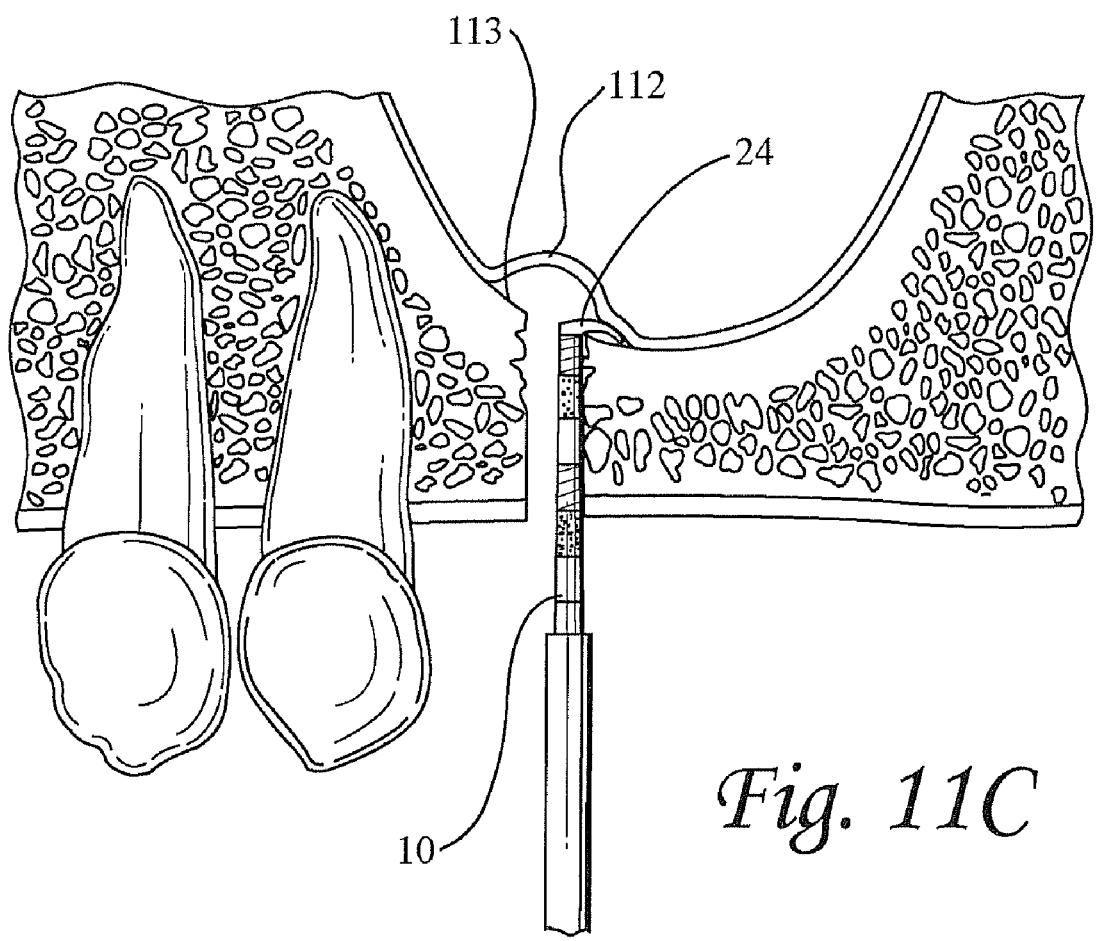

After dissecting the membrane in a local region near the hole 111, the user can retract the tool 10 from the hole 111 and rotate the tool. The operations described above are then repeated to dissect the membrane in other local regions around the hole 111 as shown in FIG. 11C. These operations allow the subantral membrane 112 to be raised relative to the floor 113 of the maxillary sinus to create a space therebetween as best shown in FIGS. 11C and 11D.

Figure 11D:
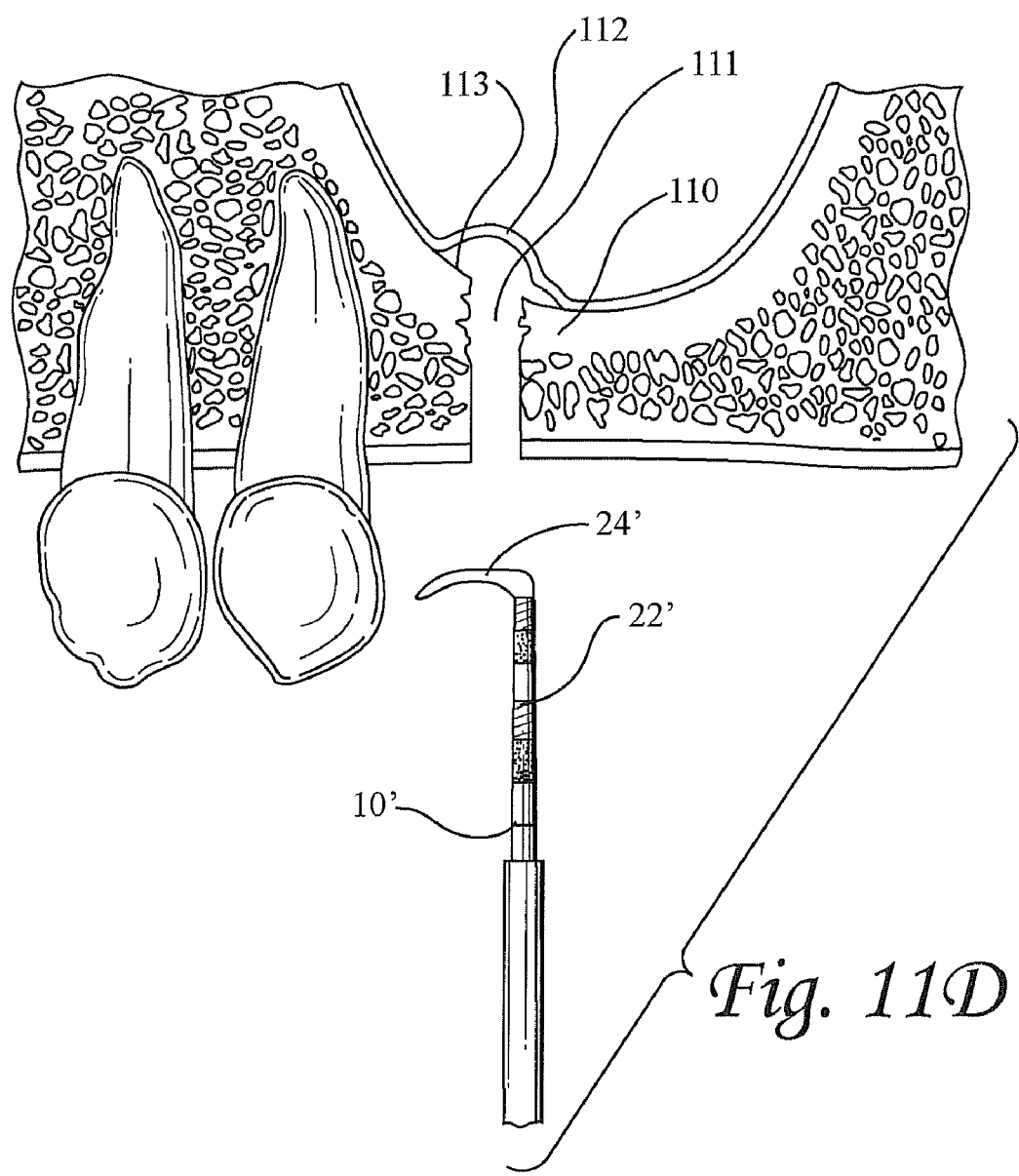
Figure 11E:
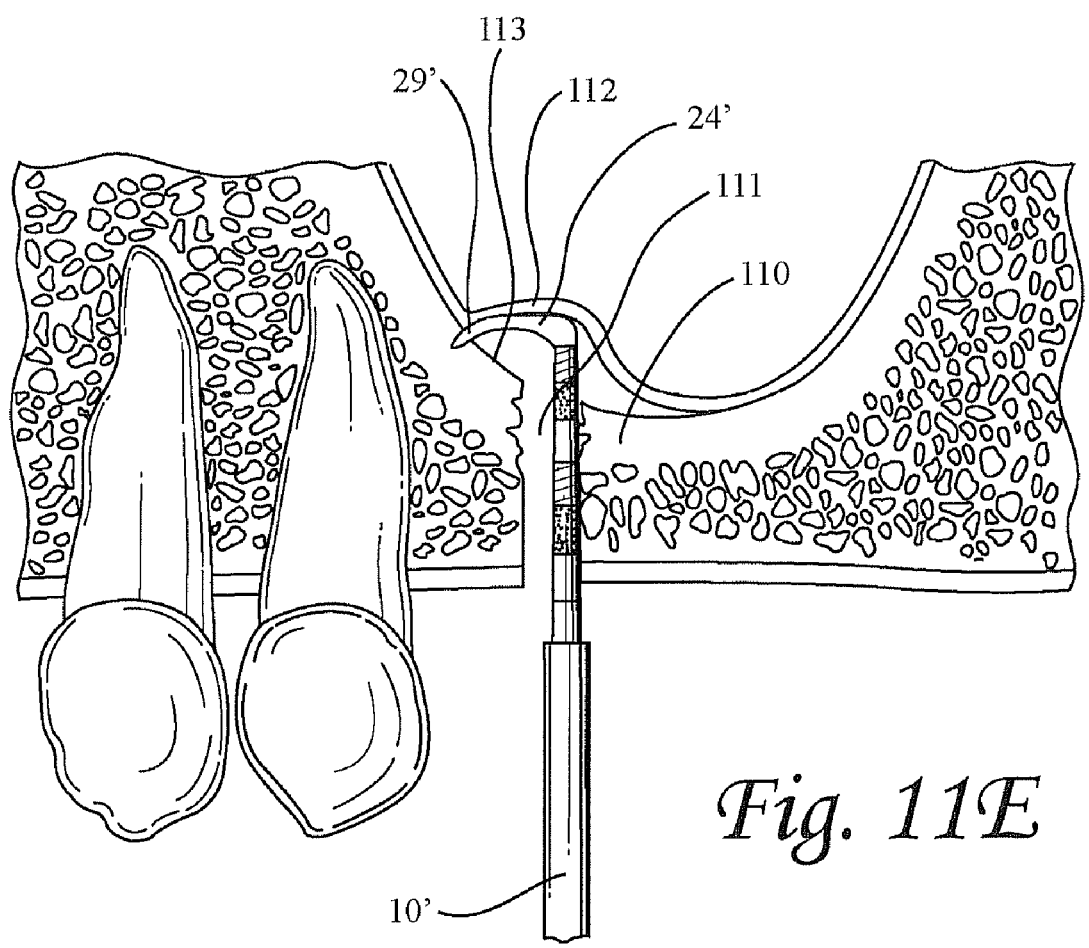
Figure 11F:
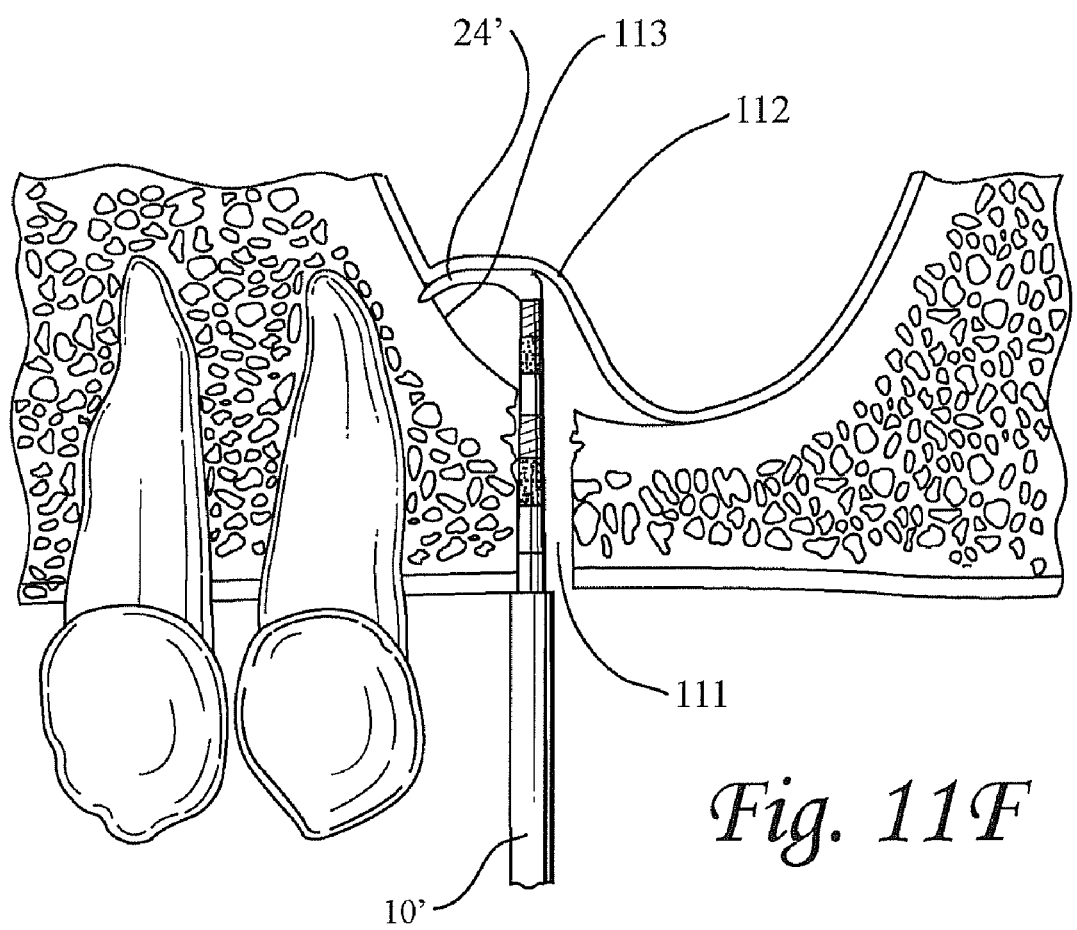

The user then selects the second tool 10' and manually manipulates the second tool 10' such that the flexible member 24' and mandrel 22' of the second tool 10' are inserted through the hole 111 and advanced upward into the space between the subantral membrane and the floor of the maxillary sinus as best shown in FIGS. 11D and 11E. The color markings on the mandrel 22' can be used to aid in depth positioning of the second tool 10'. The flexible member 24' deforms such that it bends downward toward the mandrel 22' as it passes through the hole 111 in order to allow the larger-sized member 24' to fit through the hole 111. The member 24' then flexes upward to its original position as it enters the space between the subantral membrane and the floor of the maxillary sinus as best shown in FIG. 11E. The user then manually manipulates the handle 12' (and/or possible other section(s) of the tool 10') to position the thin blade-like section 29' of the member 24' on the floor of the maxillary sinus and to subsequently move the member 24' laterally back and forth and preferably upward in strokes such that the blade-like section 29' pushes against the subantral membrane and further dissects the membrane from the floor of the maxillary sinus as shown in FIG. 11F. These strokes are continued to effectuate membrane separation at distances further and further from the edge of the hole.

Figure 11G:
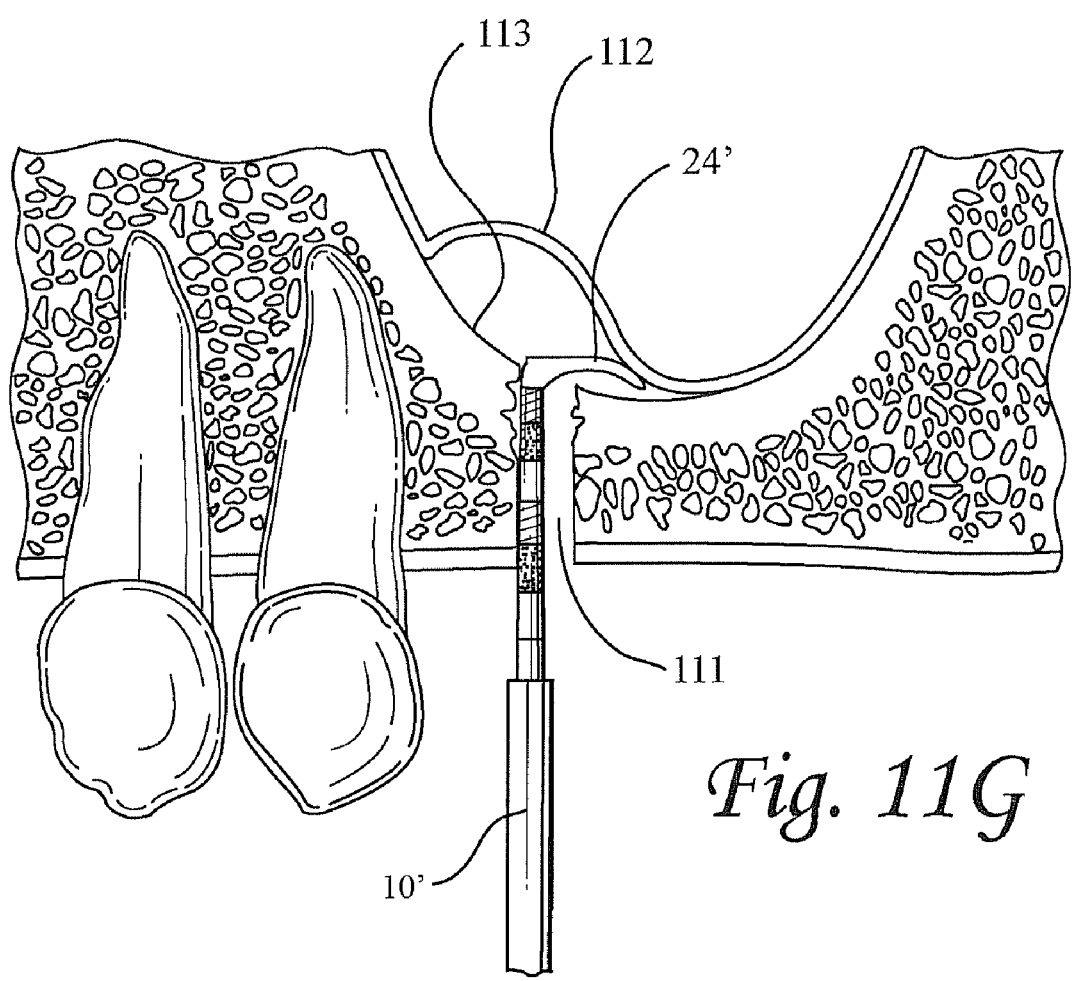
Figure 11H:
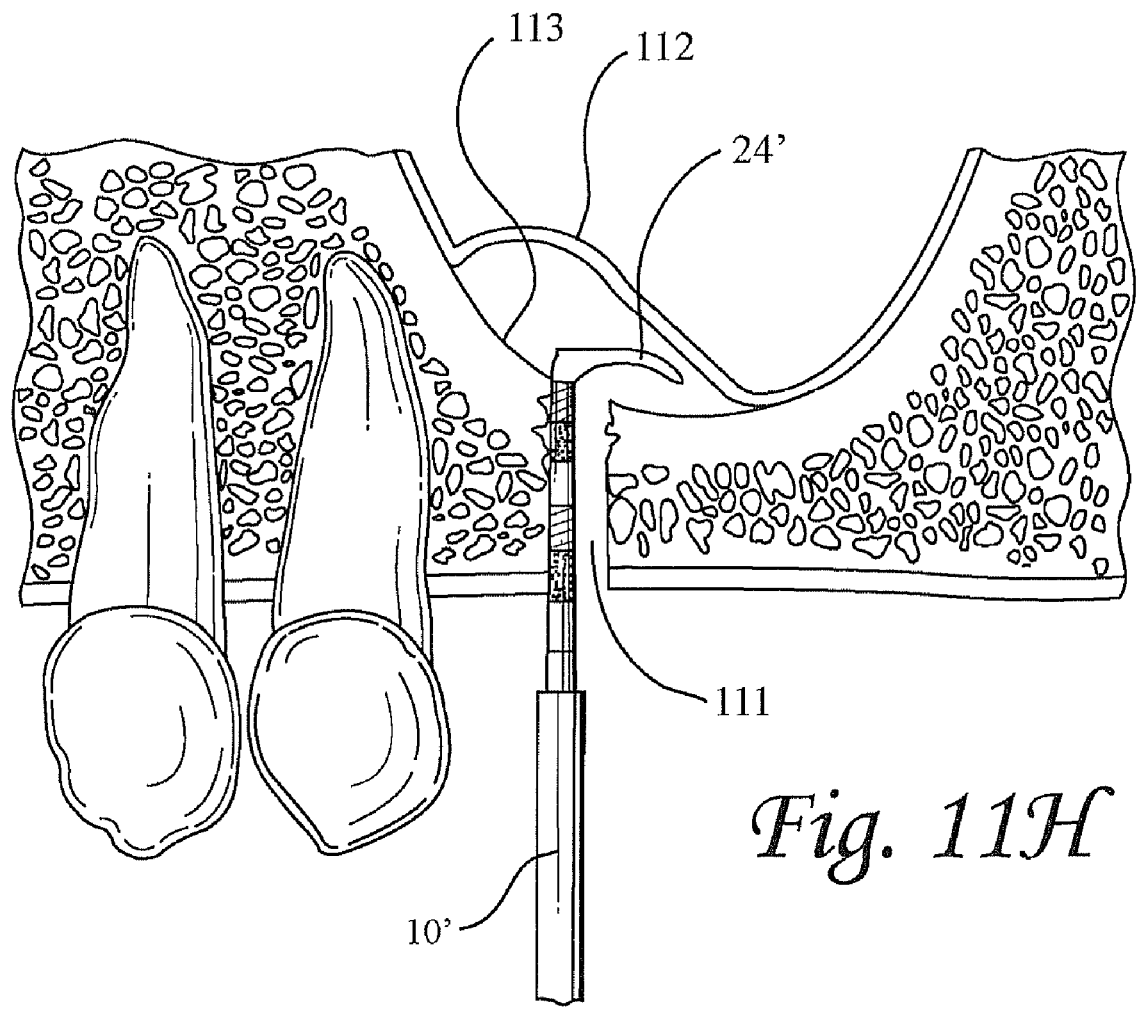
Figure 11I:
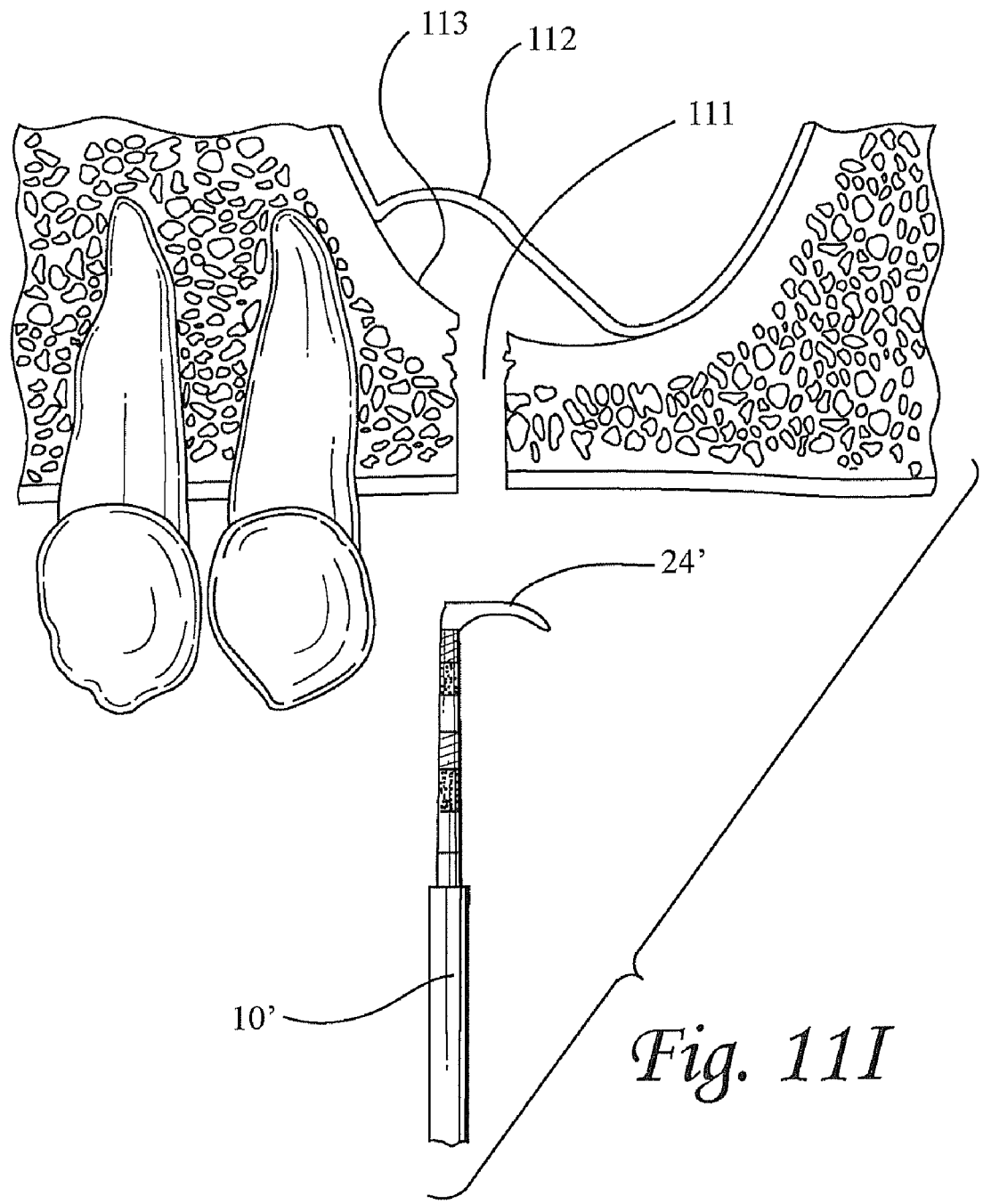
Figure 11J:
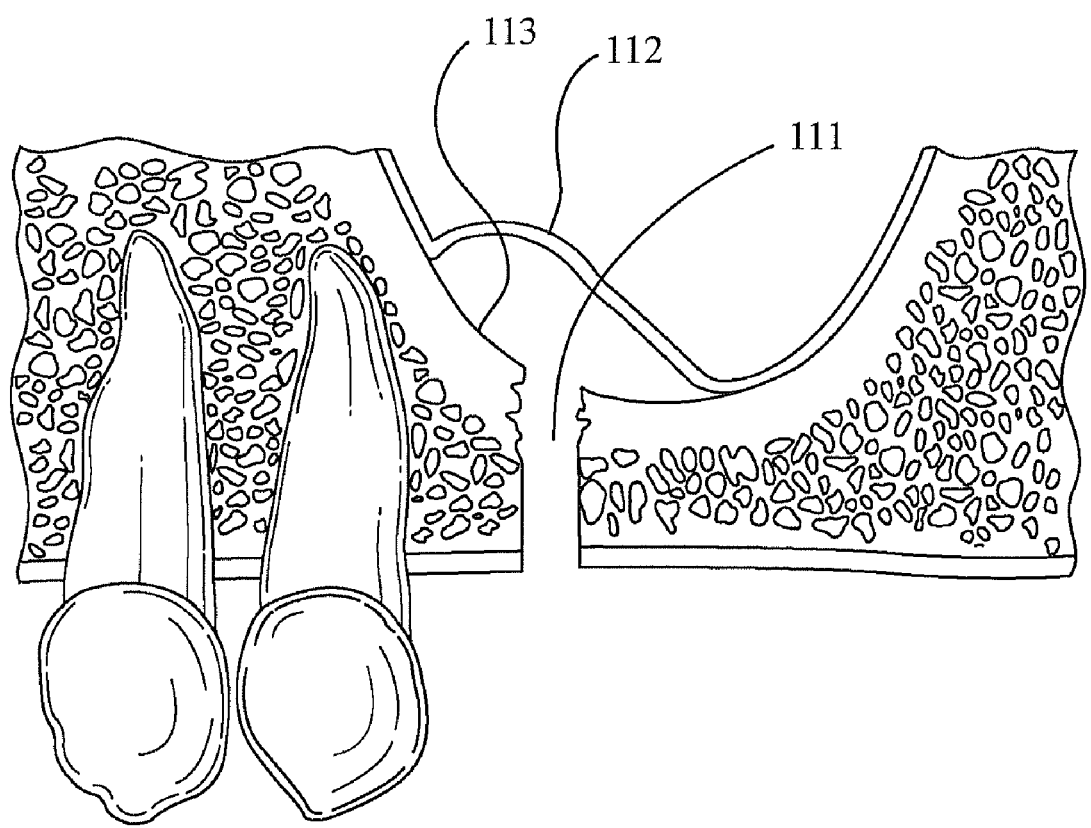

After dissecting a region of the subantral membrane with the tool 10', the user can retract the tool 10' from the hole 111. The flexible member 24' deforms such that it bends upward away from the mandrel 22' as it passes through the hole 111 in order to allow the larger-sized member 24' to fit through the hole 111. The member 24' then flexes downward to its original position as it exits the hole 111. After retraction, the tool 10' can be rotated as desired and the operations described above for the second tool 10' can be repeated to further dissect the subantral membrane in regions around the hole as shown in FIGS. 11G, 11H and 11I. These operations allow the subantral membrane 112 to be further raised relative to the floor 113 of the maxillary sinus as shown in FIG. 11J.

Figure 11K:
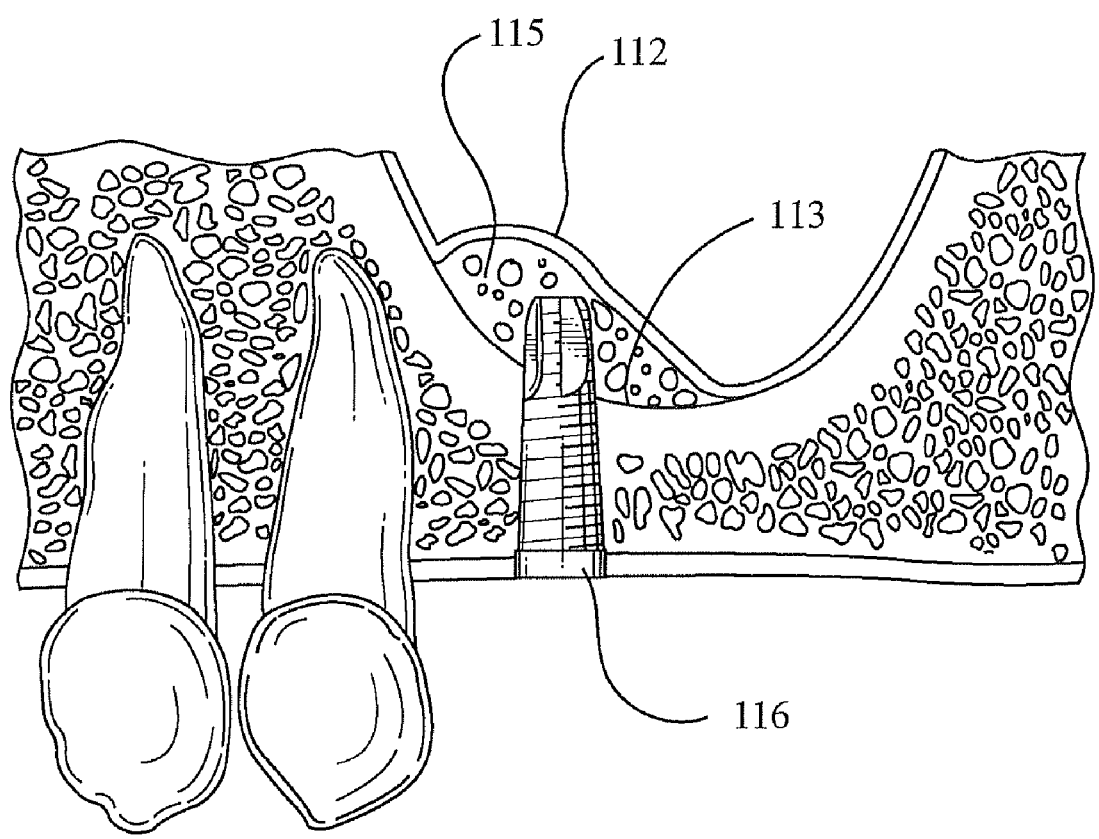

When the dissection of the subantral membrane 112 has been completed to the user's satisfaction, the user injects or otherwise packs regenerative material 115 into the space between the subantral membrane 112 and the floor 113 of the maxillary sinus. The regenerative material 115 (sometimes referred to as filler material) can be realized from natural and/or artificial bone material that will harden and bond to the surrounding bone of the anterior maxilla. In the illustrative embodiment, the regenerative material is loaded into a syringe. The distal tip of the syringe is inserted into the hole and the syringe is actuated to inject the regenerative material into the space between the subantral membrane and the floor of the maxillary sinus. A sleeve 116 is subsequently placed into the prepared site as shown in FIG. 11K. The sleeve 116 supports a prosthetic tooth (not shown) as is well known. The placement of the sleeve 116 and prosthetic tooth can occur immediately or after a predetermined delay. The delayed approach provides time for the regenerative material 115 to harden and bond to the surrounding bone of the anterior maxilla before placement of the sleeve and prosthetic tooth in order to increase the bone mass of the anterior maxilla. Alternatively, rather than using a syringe, a bone packing instrument can be use to force the filler material under the dissected and elevated subantral membrane.

Turning now to FIGS. 12-14, a third exemplary tool for elevating and dissecting the subantral membrane is shown. The tool 210 includes a handle portion 220, a mandrel 222 (substantially similar to mandrel 22), and a member 224 (substantially similar to member 24a). It is noted that the tool corresponds in function to tool 10 and that handle portion 220 is analogous to the second arm 20 thereof (and eliminates the handle 12, first arm 16 and elbow 18 thereof). The shorter, compact and preferably straight design of handle portion 220 enables the tool to be manipulated, e.g., between the thumb and forefinger, without any additional elongate extending portion of the prior embodiment which may otherwise block visualization or manipulation at the site of the procedure. The handle portion 220 includes knurls 250 which increase the tactile feedback of movement of the tool within the fingers and aid in gripping the tool. In addition, handle portion 220 includes a marker stripe 252 which visually indicates the location at which the member 224 extends, so that such can be determined when the member is hidden from the surgeon's view. At the proximal end of the handle portion, a suture loop 254 is provided to facilitate retention of the tool on a finger of a surgeon or retrieval of the tool should it become loose within the patient's mouth.

Referring now to FIGS. 15-17, a fourth exemplary tool for elevating and dissecting the subantral membrane is shown. The tool 310 includes a handle portion 320, a mandrel 322 (substantially similar to mandrel 22'), and a member 324 (substantially similar to member 24a'). It is noted that the tool corresponds in function to tool 10' and that handle portion 320 is analogous to the second arm 20' thereof (and eliminates the handle 12', first arm 16' and elbow 18' thereof). The shorter, compact and preferably straight design of handle portion 320 enables the tool to be manipulated, e.g., between the thumb and forefinger, without any additional elongate extending portion of the prior embodiment which may otherwise block visualization or manipulation at the site of the procedure. The handle portion 320 includes knurls 350 which increase the tactile feedback of movement of the tool within the fingers and aid in gripping the tool. In addition, handle portion includes a marker stripe 352 which visually indicates the direction to which the member 324 extends, so that such can be determined when the member is hidden from the surgeon's view. At the proximal end of the handle portion, a suture loop 354 is provided to facilitate retention of the tool on a finger of a surgeon or retrieval of the tool should it become loose within the patient's mouth.

Turning now to FIGS. 18 and 19, a tool 410 is provided for packing bone under the dissected and elevated subantral membrane. The tool 410 includes a handle portion 420, a mandrel 422, and a head 424. The handle and mandrel are substantially as described above with respect to tools 210 and 310. The head 424 includes a preferably frustoconical distal portion 460 and a cylindrical proximal portion 462. After the subantral membrane has been dissected and elevated, bone filler material is positioned in the drilled hole (via a syringe or otherwise) and the head of the packer is used to force the filler material into the space between the membrane and maxillary floor.

Figure 20:
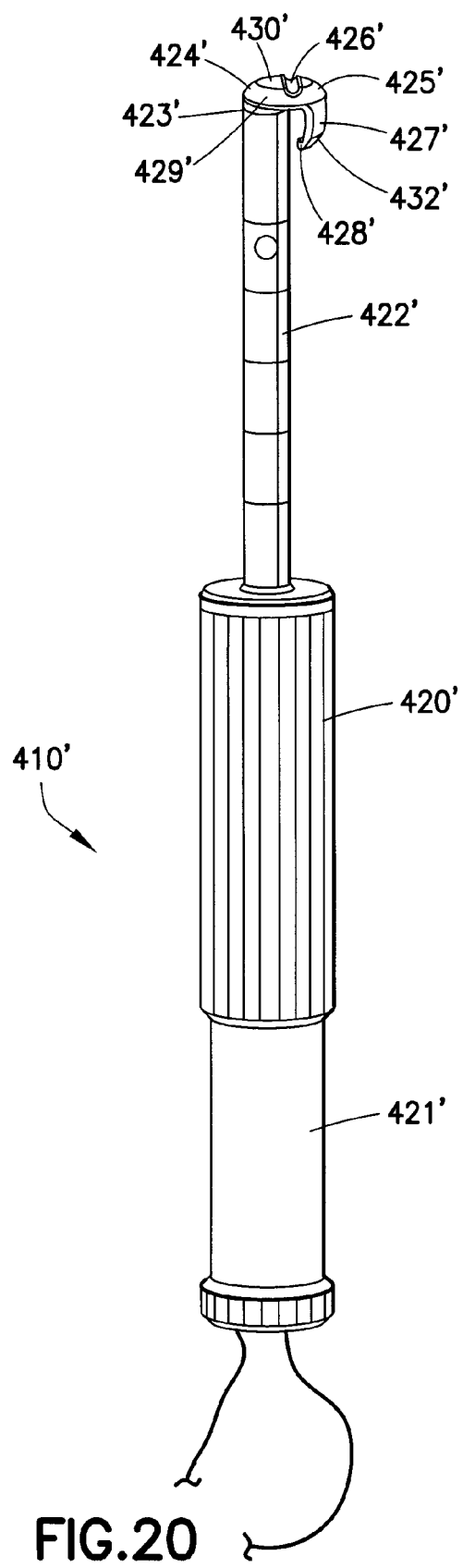
FIG. 20 is a perspective view of another embodiment of the bone packing tool.

Turning now to FIG. 20, another embodiment of a tool 410' for packing bone and bone filler material into the space between the elevated sinus membrane and the maxillary floor is shown. The tool 410' has a handle portion 420', a mandrel 422', and a head 424' disposed in an offset manner at a distal end 423' of the mandrel 422'. Handle portion 420' and mandrel 422' are substantially as described above with respect to tools 210 and 310. More particularly, the mandrel 422' is parallel to handle portion 420' and preferably has an outer diameter of 0.8-2.0 mm, a length not exceeding 30 mm and preferably between 10-15 mm, and color markings identifying spaced apart distances along the length of the mandrel 422'. These features allow the mandrel 422' to be longitudinally stable, to fit and extend through the cut hole in the maxillary bone, and to provide a visual indication to the user as to how far within the maxillary bone the tool is extended.

Figure 20B:
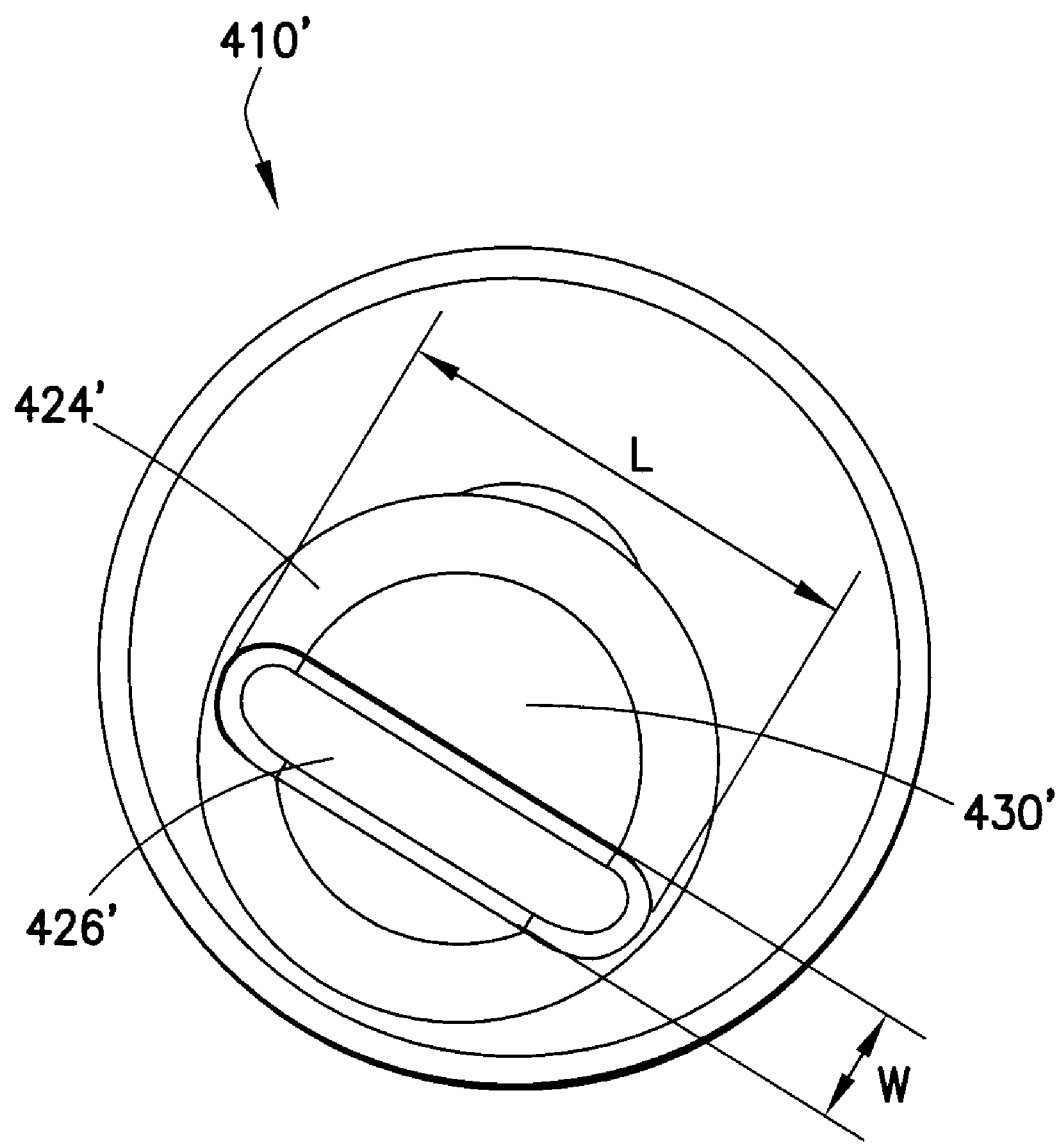
FIG. 20b is an end view of the distal end of the bone packing tool of FIG. 20.

Referring to FIGS. 20 and 20b, the head 424' of the tool 410' includes a generally flat and circular compacting surface 430' provided with a groove 426' extending across the compacting surface 430' at least partially through the depth of the compacting surface 430' to define a living hinge. The head preferably has a diameter of 3 mm±0.2 mm so that it is small enough to be inserted through a hole cut or otherwise formed in the maxillary bone and large enough to have sufficient surface area to pack bone filler and regenerative material under the lifted sinus membrane. The groove 426' preferably has a length L to width W ratio of approximately four to one. The periphery of the compacting surface includes rounded edges 429' to eliminate any sharp edges which could damage the sinus membrane during use, and particularly during compaction. The flat compacting surface 430' preferably extends substantially orthogonal relative to the central axis of the mandrel 422'.

Figure 21:
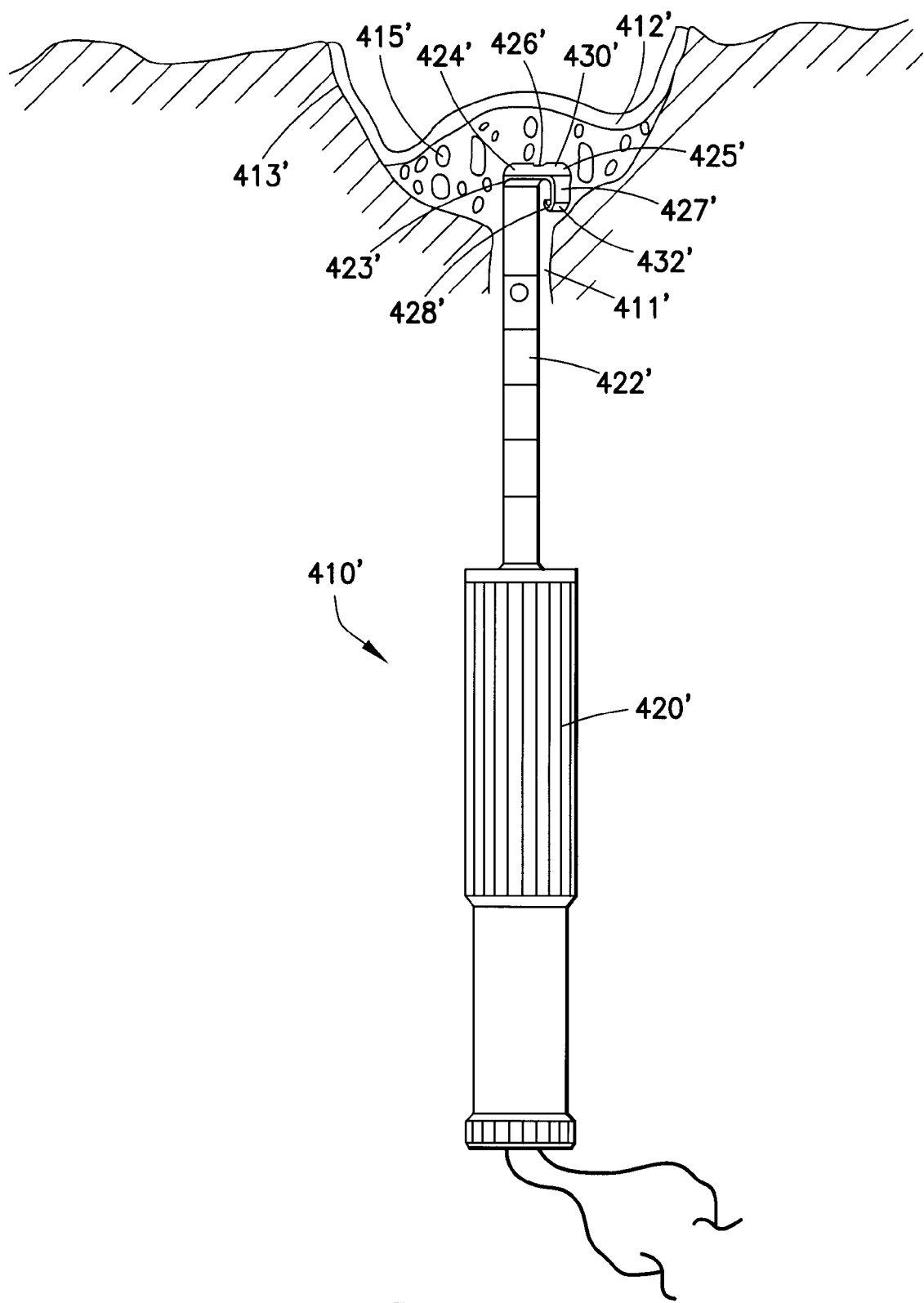
FIG. 21 is a perspective view of the bone packing tool of FIG. 20 with the head of the tool inside of the cavity formed underneath the sinus membrane.
Figure 22:
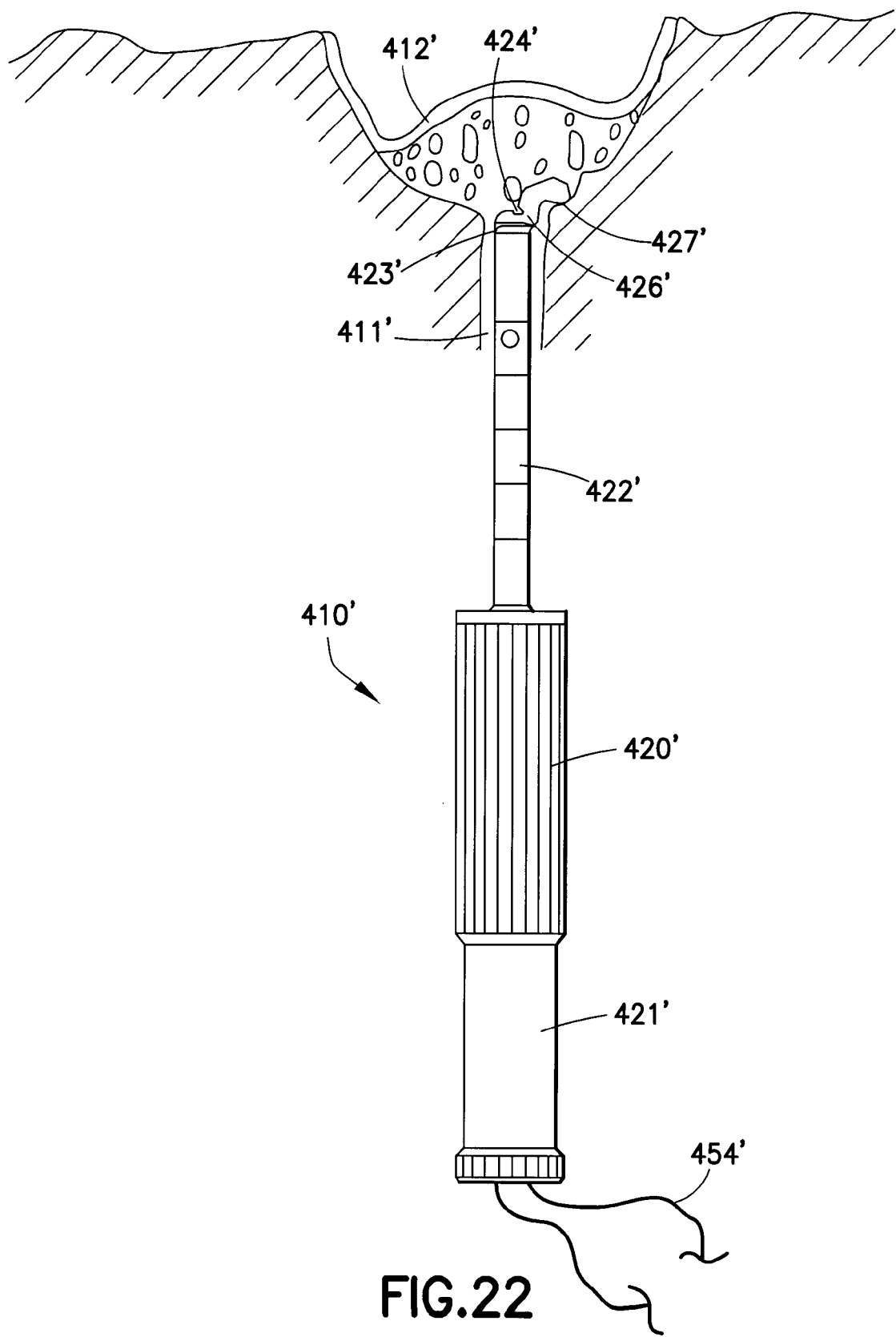
FIG. 22 is a perspective view of the bone packing tool of FIG. 20 being drawn proximally through the hole in floor of the maxillary sinus.

Referring to FIG. 21, the tool 410' is shown with the mandrel 422' partially disposed inside a hole 411' in the anterior maxilla, and the head 424' disposed inside a cavity underneath the subantral membrane 412'. The flat compacting surface 430' extends radially beyond the periphery of the distal end 423' in order to increase the accessible area that the compacting surface 430' can laterally reach to pack bone and bone filler material 415' under the sinus membrane 412'. The groove 426' (and hinge) separates the portions of surface 430' that are located over the mandrel 422' and that extend radially beyond the mandrel 422'. Referring to FIG. 22, the flexibility of the head 424' about the groove 426' allows an outer periphery 425' of the head 424' to deform and flex upward during removal from the hole 411' in the anterior maxilla in a manner similar to that described above with respect to the tooling used for the dissection and elevation of the subantral membrane 412'.

Turning back to FIG. 20, the head 424' also includes an arm 427' with a stop 428' at its end. The arm 427' projects orthogonally downward from the outer periphery 425' of the head 424' and angles inward toward the stop 428', which is disposed at or near the mandrel 422'. When the tool 410' is pushed upward inside the newly formed cavity underneath the sinus membrane 412' to pack bone filler 415', the stop 428' limits any downward bending of the head 424' about the groove 426'. For example, if the outer periphery 425' is forced downward as the tool 410' is pushed upward, the stop 428' will butt up against the mandrel 422', which prevents the head 424' from further bending downward, thus maintaining the relatively flat shape of the compacting surface 430'. The arm 427' is provided with a lower tapered surface 432' which accommodates incongruities in the maxillary floor 413' at the bottom of the newly created cavity (FIG. 21). The tapered surface 432' of the arm 427' helps to increase the lateral reach of the head 424' at or near the entrance to the cavity during bone compaction.

Turning now to FIG. 22, when the tool 410' is withdrawn from the cavity, if the arm 427' catches on any jagged edges of bone or injected bone material, then the arm 427' bends/rotates upward about the groove 426' while allowing 424' the mandrel 422' to be drawn proximally through the hole 411'. Once the tooling is moved proximally, the arm 427' will be freed and follow to allow withdrawal of the tool 410'. The groove 426' and flexibility of the head 424' thus facilitate withdrawal of the tool 410' without causing the head 424' to decapitate from the distal end 423' of the mandrel 422'. Losing the head 424' of the tool 410' during insertion, packing, or withdrawal may cause chronic sinus infections, the need for further intervention by the surgeon to remove it, and/or additional complications. The present invention helps to avoid these complications.

The head 424' is preferably realized from a polymeric material, e.g., a copolyester thermoplastic elastomer such as that sold by Ticona under the Riteflex tradename, and preferably has a shore hardness 'd' scale value between approximately 30 and 50, and more preferably 40±5 such that the head provides hardness to dissect and compact without damage to surrounding tissue.

The tool 410' further includes a suture loop 454' provided to the handle portion 420' at the opposite end relative to the head 424'. Suture loop 454' facilitates retention of the tool 410' on a finger of a surgeon for stabilization or retrieval of the tool 410' should it become loose within the patient's mouth. The suture loop 454' is shown in broken form, but may be several times the length of the tool 410' such that a surgeon can wrap the suture loop 454' around a wrist as well as a finger.

Figure 23:
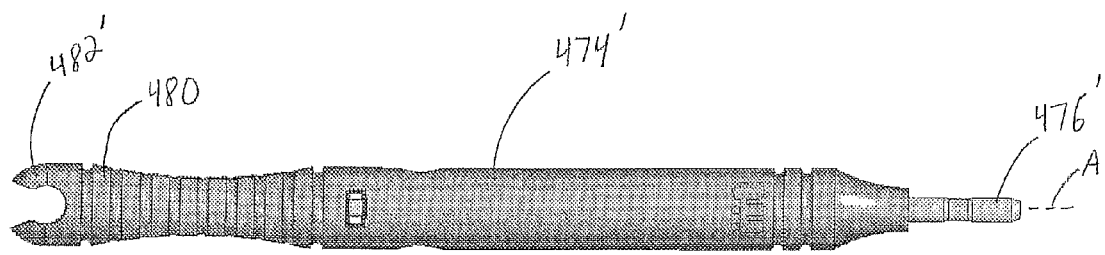
FIG. 23 is a top view of a grip stick.
Figure 24:
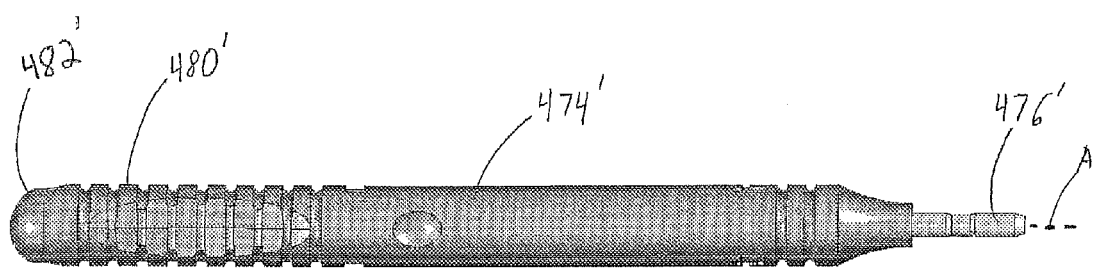
FIG. 24 is a side view of the grip stick of FIG. 23.

Referring to FIGS. 23 and 24, top and side views of a grip stick 474' are shown. The stick 474' is virtually identical to that described in International Application No. PCT/US2008/057421 (referred to therein as torque stick 774). The stick 474' has a first end 476' defining a post coaxial with axis A of the stick 474' that can be inserted into a dental tool to apply torque. For example, as disclosed in International Application PCT/US2008/057421, first end post 476' is inserted into a knob of a maxillary bone cutting device to increase torque and thereby facilitate cutting through the bone. Stick 474' includes a second end 480' provided with a clip 482' for engaging a circumferential recess 421' (FIG. 20) in the handle 420' of the tool 410'. The grip stick 474' is oriented such that the clip 482' at the second end 480' is positioned to clip onto the recess 421' in the handle 420' of the tool 410'.

Figure 25:
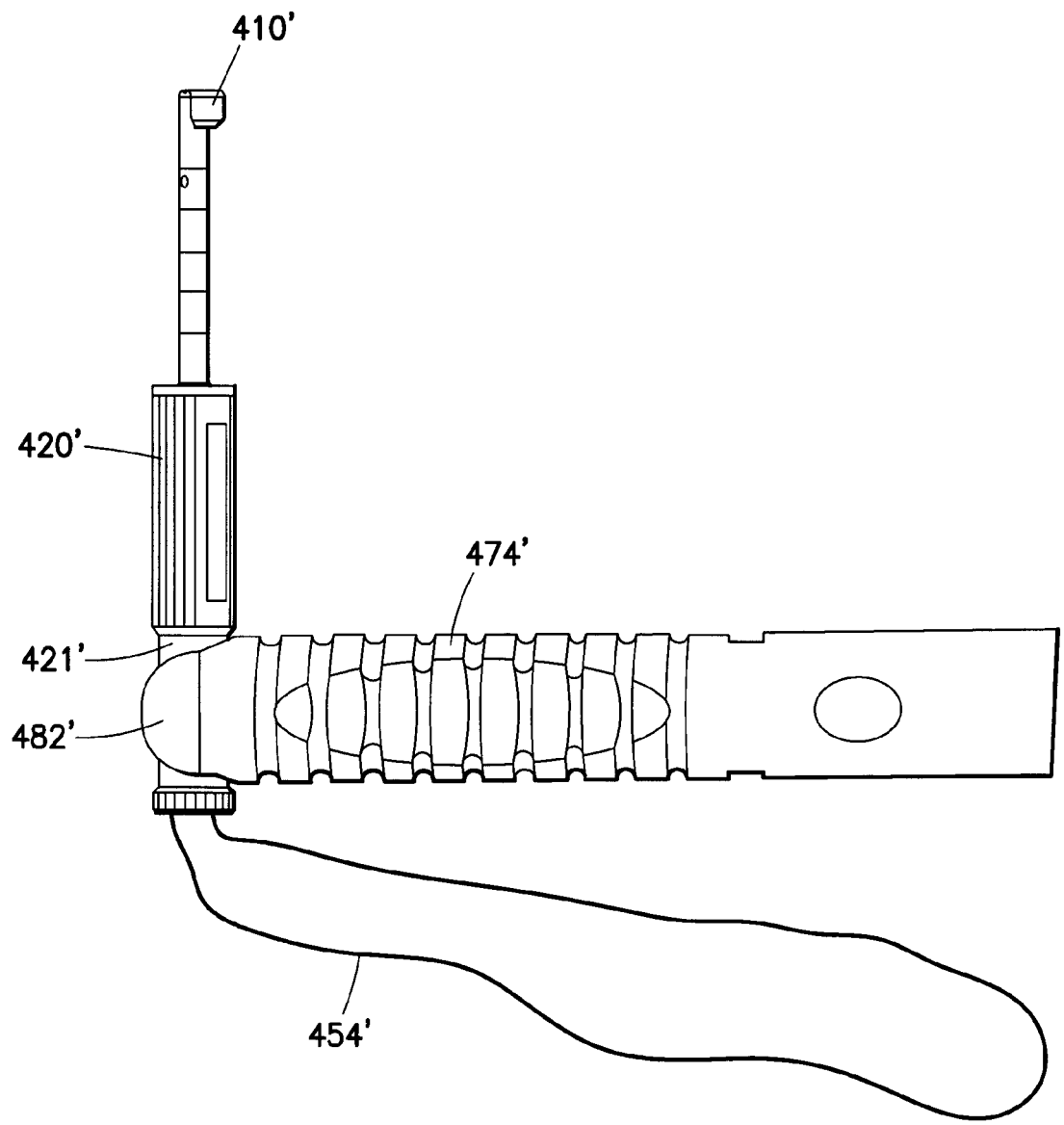
FIG. 25 is a view of the grip stick of FIG. 23 attached to the bone packing tool of FIG. 20.

Referring to FIG. 25, the grip stick 474' is shown attached to the tool 410' at the recess 421'. The clip 482' preferably snaps onto the handle portion 420' at the recess 421', thus allowing the stick 474' to be used as an additional handle for manipulating or stabilizing the tool 410' within a patient. The handle portion 420' is rotatable within the clip 482', which, used in conjunction with the suture loop 454', facilitates a stabilized and controlled use of the bone packer 410'.

There have been described and illustrated herein several embodiments of tools and associated methods for dissection and elevation of the subantral membrane. While particular embodiments of the invention have been described, it is not intended that the invention be limited thereto, as it is intended that the invention be as broad in scope as the art will allow and that the specification be read likewise. Thus, while particular shapes and dimensions have been disclosed, it will be appreciated that other shapes and dimensions can be used as well. For example, the handles can possibly include ergonomic shapes commonly used in toothbrushes or other dental tools. In another example, the distal members of the tools can possibly have other oblong shapes or other complex shapes. In addition, while particular structures and configurations have been disclosed for hand-held support of relatively thin members that dissect and elevate the subantral membrane, it will be understood that other structures and configurations can be used. Moreover, while particular methodologies have been disclosed for dissecting and elevating the subantral membrane, it will be appreciated that the tools described herein can be used for other sinus elevation methods. It will therefore be appreciated by those skilled in the art that yet other modifications could be made to the provided invention without deviating from its spirit and scope as claimed.

What is claimed is:

1. A device for insertion through a hole created in the floor of the maxillary sinus, the device comprising:
    a) a handle;
    b) an elongate mandrel extending from said handle, said mandrel having a distal end, a central axis, and a periphery and a length, said length not exceeding 30 mm; and
    c) a head mounted to said distal end of said mandrel, said head having an upper surface opposite a lower surface, said upper surface defined by a distal side of said head and said lower surface defined by a proximal side of said head, said upper surface extending radially outward relative to said central axis of said mandrel, said upper surface defining a groove recessed into said upper surface and offset from said central axis with an outer peripheral portion of said upper surface extending beyond said groove, said groove defining a hinge across said head that allows for deformation of said head so that said outer peripheral portion can flex upward about said groove relative to said mandrel,
    wherein, said head has a cross-wise dimension parallel to said groove not exceeding 3.2 mm and is realized from a material having a shore hardness d scale value in the range of 30 to 50.

2. A device according to claim 1, wherein:
said head is realized from a polymeric material.

3. A device according to claim 1, wherein:
said upper surface surrounding said groove is smooth.

4. A device according to claim 1, wherein:
said upper surface surrounding said groove is flat.

5. A device according to claim 1, wherein:
said mandrel includes a plurality of colored indicia along said length.

6. A device according to claim 1, wherein:
said handle and said mandrel are parallel.

7. A device according to claim 1, wherein:
said head defines a circular shape.

8. A device according to claim 1, further comprising:
an arm integrally formed with said head and a stop integrally formed with said arm, said arm projecting orthogonally downward from said outer peripheral portion, and said stop directed toward and disposed adjacent said mandrel, whereby said stop limits downward flexing and rotation of said outer peripheral portion about said groove.

9. A device according to claim 8, wherein:
said arm includes a tapered surface opposite said upper surface.

10. A device according to claim 1, further comprising:
a grip stick mountable to said handle, said grip stick having a clip at a first end that engages with a proximal end of said handle such that said grip stick is oriented orthogonal relative to said central axis of said mandrel.

11. A device according to claim 10, wherein:
said grip stick has a central axis and a second end opposite said first end, said second end defining a post coaxial with said central axis.

12. A device according to claim 1, wherein:
said handle includes a circumferential recess at which said clip is mountable about said handle.

13. A device according to claim 1, wherein:
said upper surface is circular in shape with a diameter between 2.8 mm and 3.2 mm.

14. A device according to claim 1, further comprising:
a stop that limits deformation of said head provided by said hinge when said outer peripheral portion flexes downward about said groove relative to said mandrel.

15. A device according to claim 14, further comprising:
an arm integrally formed with said head, said arm projecting downward from said outer peripheral portion and terminating at said stop.

16. A device according to claim 15, wherein:
said arm includes a tapered surface opposite said upper surface.

17. A device according to claim 15, wherein:
said arm projects orthogonally downward from said outer peripheral portion, and said stop is directed toward and disposed adjacent said mandrel.

18. A device according to claim 14, wherein:
said stop is configured to interface to said mandrel in order to limit deformation of said head provided by said hinge when said outer peripheral portion flexes downward about said groove relative to said mandrel.

19. A system for compacting bone material near the floor of the maxillary sinus, the device comprising:
 a) a tool including,
  i) a handle having a circumferential recess,
  ii) an elongate mandrel extending from said handle, said mandrel having a distal end, a central axis, and a periphery and a length, said length not exceeding 30 mm, and
  iii) a head mounted to said distal end of mandrel, said head having an upper surface opposite a lower surface, said upper surface defined by a distal side of said head and said lower surface defined by a proximal side of said head, said upper surface defining a groove recessed into said upper surface and offset from said central axis with an outer peripheral portion of said upper surface extending beyond said groove, said groove defining a hinge across said head that allows for deformation of said head so that said outer peripheral portion can flex upward about said groove relative to said mandrel,
  wherein, said head has a minimum cross-wise dimension not exceeding 3.2 mm and is realized from a material having a shore hardness d scale value in the range of 30 to 50; and
 b) a grip stick including a clip at a first end, said clip removably mountable to said handle at said circumferential recess, wherein when said grip stick is mounted to said handle at said circumferential recess, said grip stick is oriented orthogonal relative to said central axis of said mandrel.

20. A device according to claim 19, wherein:
said grip stick has a central axis and a second end opposite said first end, said second end defining a post coaxial with said central axis.

21. A kit of tools for use in preparing the subantral membrane and a space formed therebeneath for receiving a dental implant, comprising:
 a) a dissection tool for dissecting a subantral membrane from the floor of the maxillary sinus, including,
  i) a handle,
  ii) an elongate mandrel extending from said handle, said mandrel having a distal end, a central axis, and a periphery and a length, said length not exceeding 30 mm, and
  iii) a head mounted to said distal end of said mandrel, said head having an upper surface opposite a lower surface, said upper surface defined by a distal side of said head and said lower surface defined by a proximal side of said head, said upper surface extending radially outward relative to said central axis of said mandrel, said upper surface tapering in thickness to a free end suitable for dissecting the subantral membrane from the maxillary sinus floor,
  wherein said head has a cross-wise dimension parallel to said groove not exceeding 3.2 mm and is realized from a material having a shore hardness d scale value in the range of 30 to 50; and
 b) a packing device for packing bone and bone substitute materials under a subantral membrane, including,
  i) a handle,
  ii) an elongate mandrel extending from said handle, said mandrel having a distal end, a central axis, and a periphery and a length, said length not exceeding 30 mm, and
  iii) a head mounted to said distal end of said support element, said head having an upper surface opposite a lower surface, said upper surface defined by a distal side of said head and said lower surface defined by a proximal side of said head, said upper surface extending radially outward relative to said central axis of said mandrel, said upper surface for compacting bone in a direction opposite of said handle,
  wherein said head has a cross-wise dimension parallel to said groove not exceeding 3.2 mm and is realized from a material having a shore hardness d scale value in the range of 30 to 50; and
  wherein at least one of said upper surface of said head of said dissection tool and said upper surface of said head of said packing device defines a groove recessed into the respective upper surface and offset from said central axis of the respective mandrel with an outer peripheral portion of the respective upper surface extending beyond said groove, said groove defining a hinge across said head that allows for deformation of said head so that said outer peripheral portion can flex upward about said groove relative to the respective mandrel.

22. A kit according to claim 21, wherein:
wherein said upper surface of said packing device defines a corresponding groove recessed into the respective upper surface and offset from said central axis of the mandrel of the packing device, and said packing device further includes a stop that limits deformation of the head of the packing device provided by said hinge when said outer peripheral portion flexes downward about said groove relative to said mandrel of said packing device.

23. A kit according to claim 21, wherein:
both said upper surface of said dissection tool and said upper surface of said packing device each define a corresponding groove recessed into the respective upper surface and offset from said central axis of the respective mandrel.

24. A device for insertion through a hole created in the floor of the maxillary sinus, the device comprising:
 a) a handle;
 b) an elongate mandrel extending from said handle, said mandrel having a distal end, a central axis, and a periphery and a length, said length not exceeding 30 mm;
 c) a head mounted to said distal end of said mandrel, said head having an upper surface opposite said handle, said upper surface extending radially outward relative to said central axis of said mandrel, said upper surface defining a groove, and said upper surface having an outer peripheral portion, said outer peripheral portion being deformable about said groove so that said outer peripheral portion can flex upward about said groove relative to said mandrel,
  wherein, said head has a cross-wise dimension parallel to said groove not exceeding 3.2 mm and is realized from a material having a shore hardness d scale value in the range of 30 to 50; and
 d) an arm integrally formed with said head and a stop integrally formed with said arm, said arm projecting orthogonally downward from said outer peripheral portion, and said stop directed toward and disposed adjacent said mandrel, whereby said stop limits downward flexing and rotation of said outer peripheral portion about said groove.

25. A device according to claim 24, wherein:
said arm includes a tapered surface opposite said upper surface.

* * * * *